United States Patent [19]
Thompson et al.

[11] Patent Number: 6,152,920
[45] Date of Patent: *Nov. 28, 2000

[54] SURGICAL METHOD AND APPARATUS FOR POSITIONING A DIAGNOSTIC OR THERAPEUTIC ELEMENT WITHIN THE BODY

[75] Inventors: Russell B. Thompson, Los Altos; Edward J. Snyder, San Jose; Sidney D. Fleischman, Menlo Park; James G. Whayne, Saratoga; Thomas R. Jenkins, Oakland, all of Calif.

[73] Assignee: EP Technologies, Inc., San Jose, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/949,117

[22] Filed: Oct. 10, 1997

[51] Int. Cl.⁷ ..................................................... A61B 17/39
[52] U.S. Cl. ............................... 606/41; 606/46; 606/47; 606/49; 600/374; 600/393; 607/99
[58] Field of Search ................................. 606/41, 46, 47, 606/49; 607/99; 600/374, 393; 604/105

[56] References Cited

U.S. PATENT DOCUMENTS

| | | |
|---|---|---|
| 463,785 | 11/1891 | Connable . |
| 3,316,913 | 5/1967 | Swenson . |
| 3,999,555 | 12/1976 | Person . |
| 4,011,872 | 3/1977 | Komiya ..................................... 606/47 |
| 4,181,131 | 1/1980 | Ogiu . |
| 4,306,561 | 12/1981 | de Medinaceli . |
| 4,493,320 | 1/1985 | Treat . |
| 4,517,975 | 5/1985 | Garito et al. . |
| 4,523,679 | 6/1985 | Paikoff et al. . |
| 4,532,924 | 8/1985 | Auth et al. . |
| 4,565,200 | 1/1986 | Cosman . |
| 4,567,890 | 2/1986 | Ohta et al. . |
| 4,681,122 | 7/1987 | Winters et al. . |
| 4,765,331 | 8/1988 | Petruzzi et al. . |
| 4,800,899 | 1/1989 | Elliott . |
| 4,920,978 | 5/1990 | Colvin . |
| 5,002,561 | 3/1991 | Fisher . |
| 5,013,312 | 5/1991 | Parins et al. . |
| 5,078,716 | 1/1992 | Doll . |
| 5,088,997 | 2/1992 | Delahuerga et al. . |
| 5,108,391 | 4/1992 | Flachenecker et al. . |
| 5,122,137 | 6/1992 | Lennox . |
| 5,131,379 | 7/1992 | Sewell, Jr. . |
| 5,244,462 | 9/1993 | Delahuerga et al. . |
| 5,249,121 | 9/1993 | Baum et al. . |
| 5,263,493 | 11/1993 | Avitall . |

(List continued on next page.)

FOREIGN PATENT DOCUMENTS

| | | |
|---|---|---|
| 0 484 671 A2 | 5/1992 | European Pat. Off. . |
| 0 584 787 A1 | 8/1992 | European Pat. Off. . |
| 4425195 | 11/1995 | Germany . |
| 19503702 | 8/1996 | Germany . |
| WO 93/08755 | 5/1993 | WIPO . |
| WO 95/10236 | 4/1995 | WIPO . |
| WO 96/37156 | 11/1996 | WIPO . |
| WO 97/17027 | 5/1997 | WIPO . |
| WO 97/30644 | 8/1997 | WIPO . |
| WO 97/41793 | 11/1997 | WIPO . |
| WO98/17187 | 4/1998 | WIPO . |
| WO99/04696 | 2/1999 | WIPO . |

OTHER PUBLICATIONS

PCT International Search Report—PCT/US98/21357.

*Primary Examiner*—Lee Cohen
*Attorney, Agent, or Firm*—Henricks, Slavin & Holmes LLP

[57] ABSTRACT

A surgical device including a relatively short shaft, a bendable spline assembly associated with the distal end of the shaft and having a predetermined configuration, the spline assembly being adapted to collapse in response to an application of an external force and to expand to the predetermined configuration in response to a withdrawal of the external force, and an operative element associated with the bendable spline assembly.

25 Claims, 20 Drawing Sheets

U.S. PATENT DOCUMENTS

| | | |
|---|---|---|
| 5,277,201 | 1/1994 | Stern . |
| 5,290,286 | 3/1994 | Parins . |
| 5,318,564 | 6/1994 | Eggers . |
| 5,324,288 | 6/1994 | Billings et al. . |
| 5,342,356 | 8/1994 | Ellman et al. . |
| 5,370,650 | 12/1994 | Tovey et al. . |
| 5,381,896 | 1/1995 | Simons . |
| 5,383,876 | 1/1995 | Nardella . |
| 5,401,274 | 3/1995 | Kusunoki . |
| 5,403,342 | 4/1995 | Tovey et al. . |
| 5,415,656 | 5/1995 | Tihon et al. . |
| 5,423,810 | 6/1995 | Goble et al. . |
| 5,437,664 | 8/1995 | Cohen et al. . |
| 5,437,665 | 8/1995 | Munro . |
| 5,443,463 | 8/1995 | Stern et al. . |
| 5,445,638 | 8/1995 | Rydell et al. . |
| 5,451,224 | 9/1995 | Goble et al. . |
| 5,456,699 | 10/1995 | Armstrong . |
| 5,486,173 | 1/1996 | Vancaillie . |
| 5,505,730 | 4/1996 | Edwards . |
| 5,562,720 | 10/1996 | Stern et al. . |
| 5,569,242 | 10/1996 | Lax et al. . |
| 5,571,098 | 11/1996 | Domankevitz et al. . |
| 5,624,454 | 4/1997 | Palti . |
| 5,658,280 | 8/1997 | Issa . |
| 5,681,282 | 10/1997 | Eggers et al. . |
| 5,683,366 | 11/1997 | Eggers et al. . |
| 5,687,723 | 11/1997 | Avitall . |
| 5,688,266 | 11/1997 | Edwards et al. . |
| 5,688,268 | 11/1997 | Billings . |
| 5,697,536 | 12/1997 | Eggers et al. . |
| 5,697,882 | 12/1997 | Eggers et al. . |
| 5,697,909 | 12/1997 | Eggers et al. . |
| 5,702,371 | 12/1997 | Bierman . |
| 5,702,438 | 12/1997 | Avitall ................................. 600/374 |
| 5,730,704 | 3/1998 | Avitall ................................. 600/374 |
| 5,733,280 | 3/1998 | Avitall . |
| 5,738,683 | 4/1998 | Osypka . |
| 5,746,748 | 5/1998 | Steinberg . |
| 5,788,688 | 8/1998 | Bauer et al. . |
| 5,823,956 | 10/1998 | Roth et al. ........................... 606/41 |
| 5,830,183 | 11/1998 | Krieger . |
| 5,833,690 | 11/1998 | Yates et al. . |
| 5,836,947 | 11/1998 | Fleischman et al. ................. 606/41 |
| 5,868,742 | 2/1999 | Manes et al. . |
| 5,895,386 | 4/1999 | Odell et al. . |
| 5,908,420 | 6/1999 | Parins et al. . |

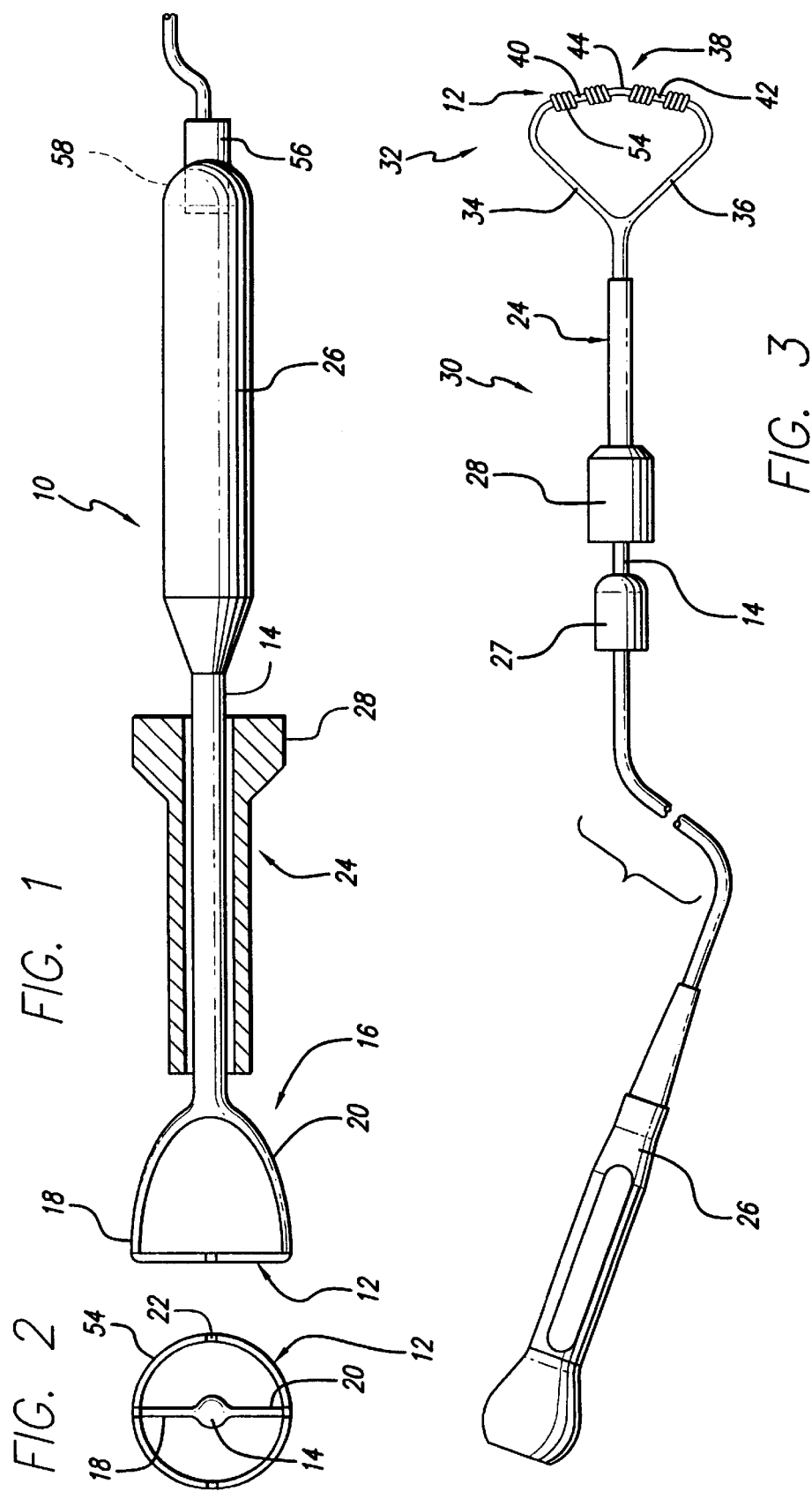

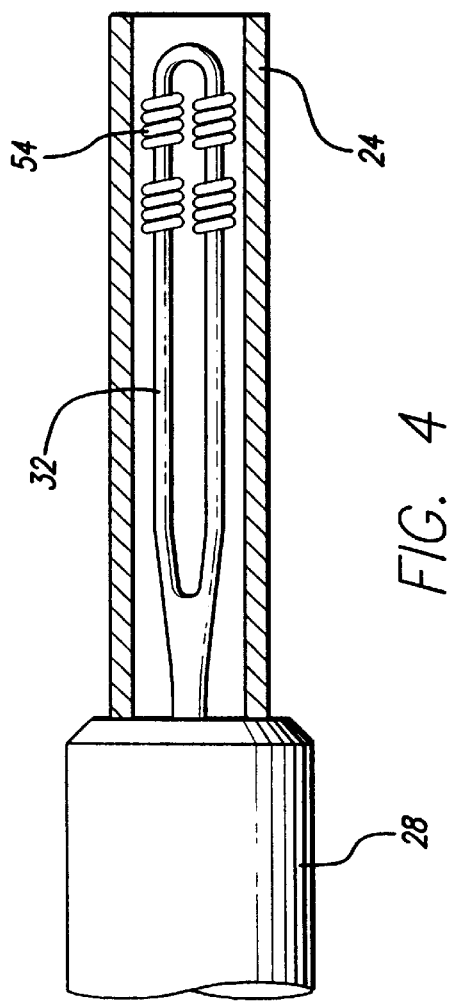
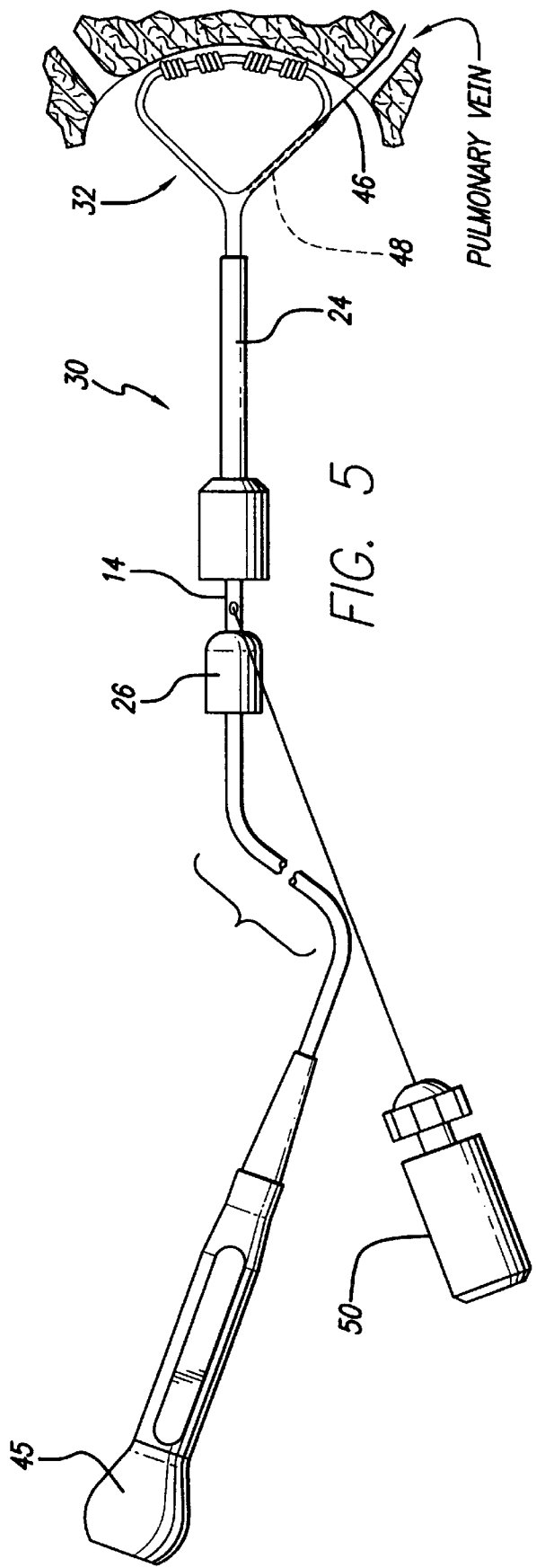

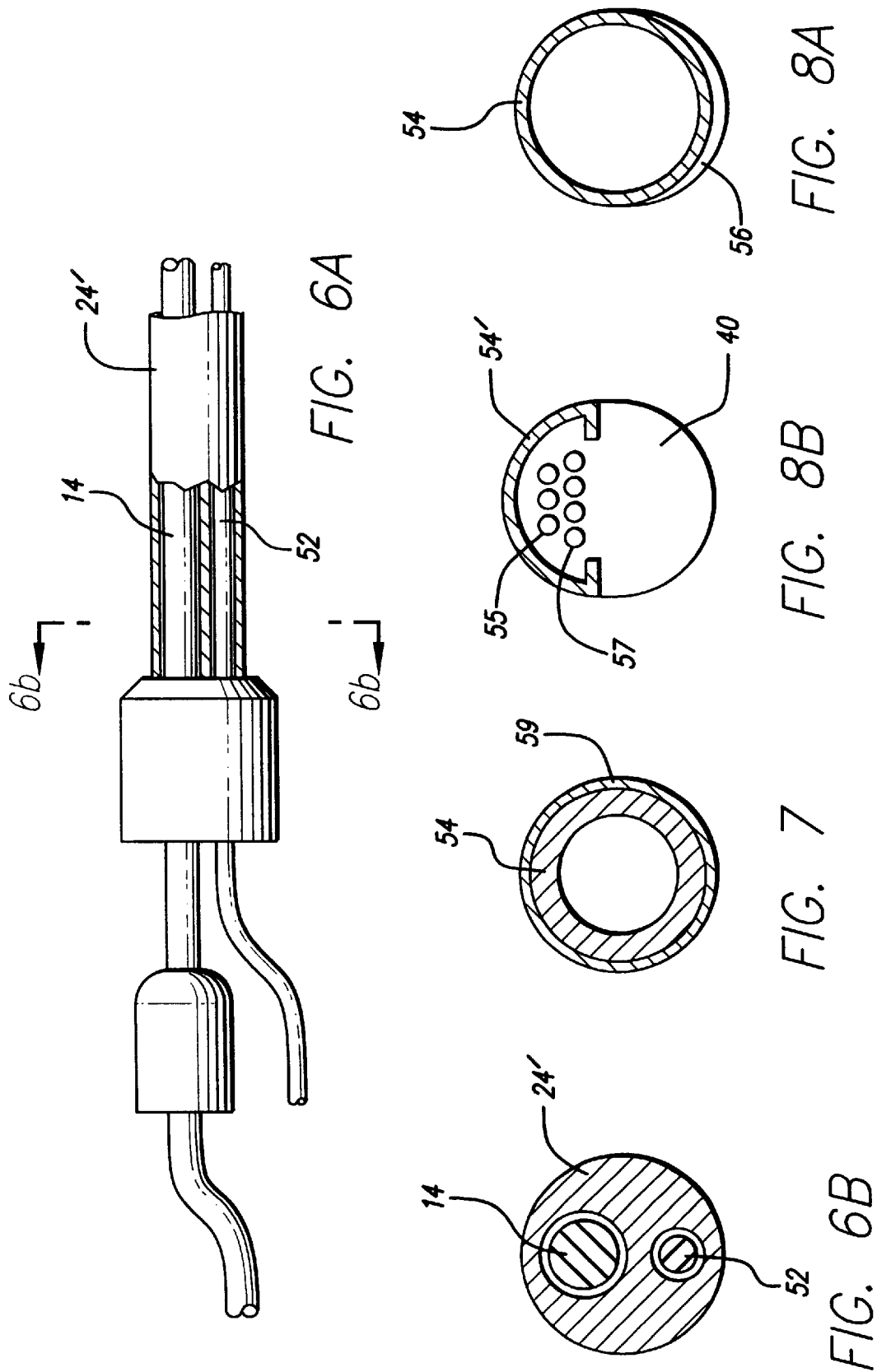

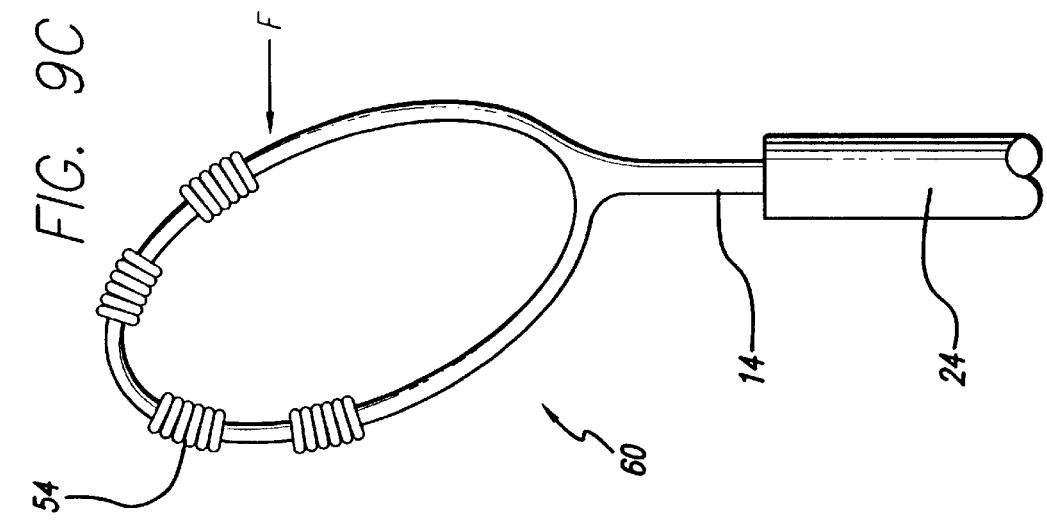
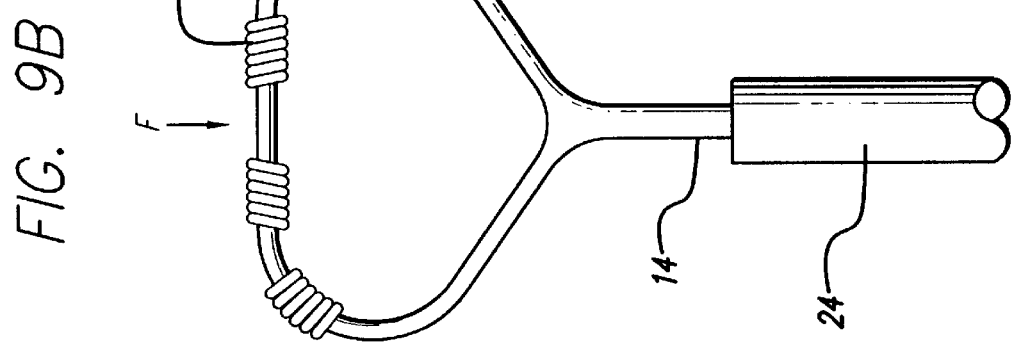
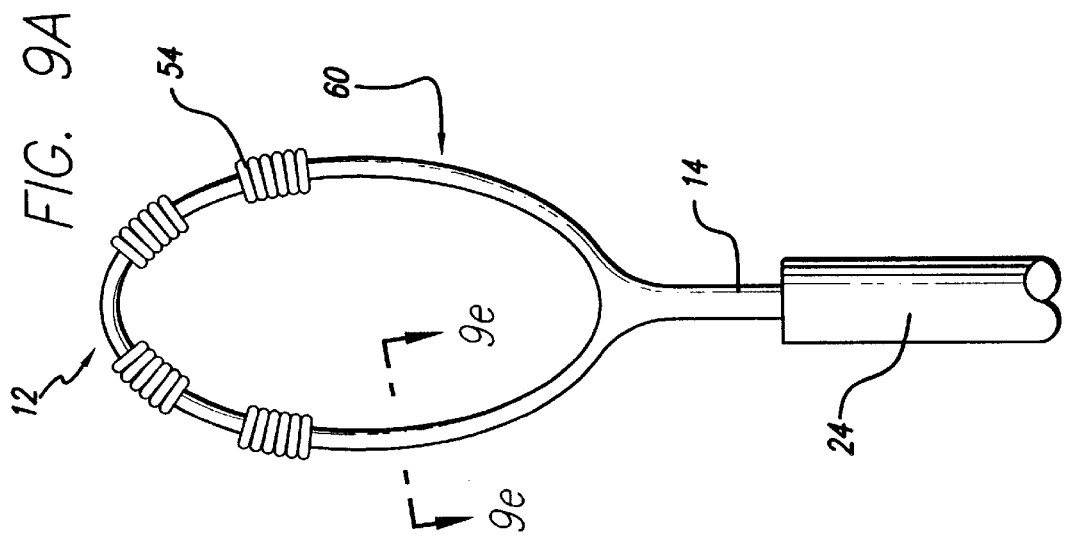

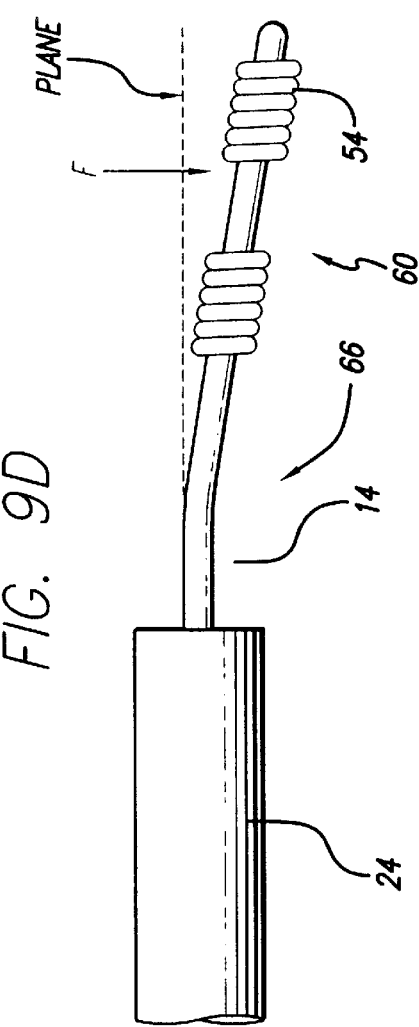
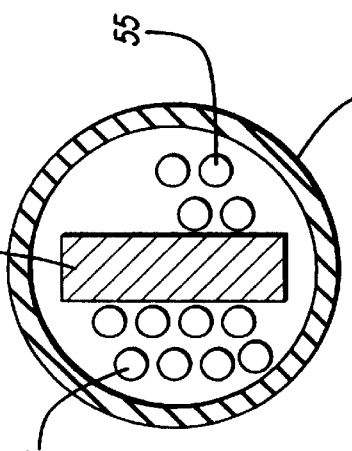
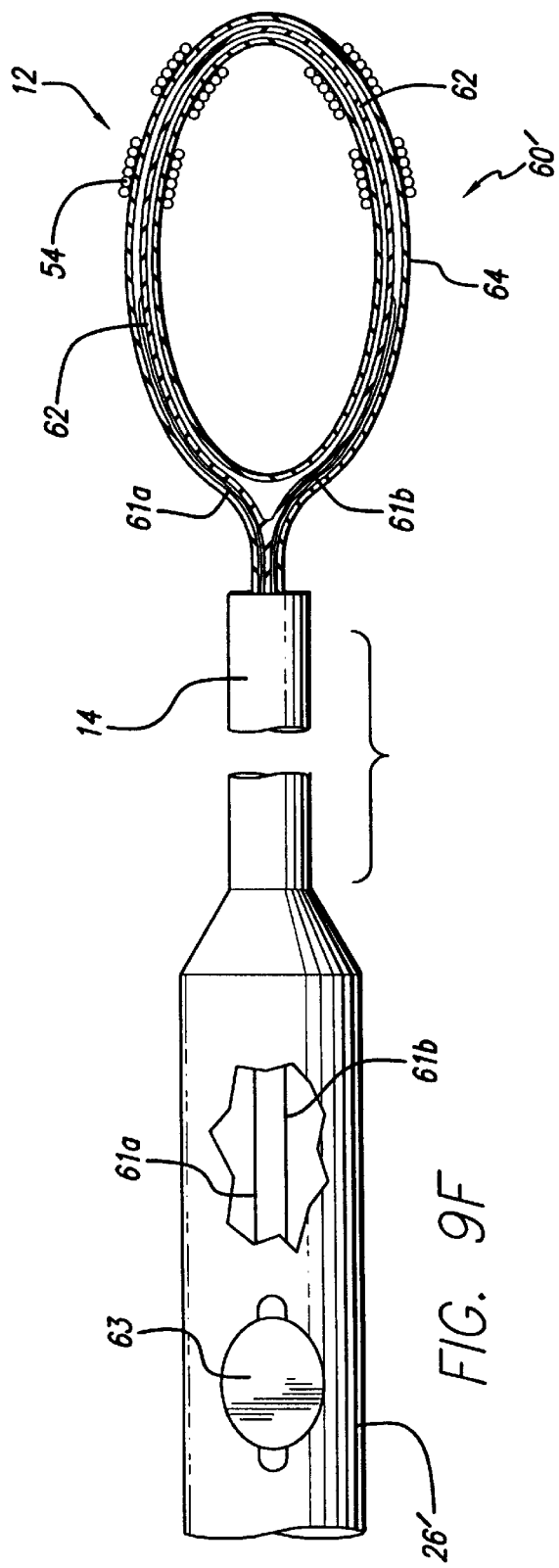

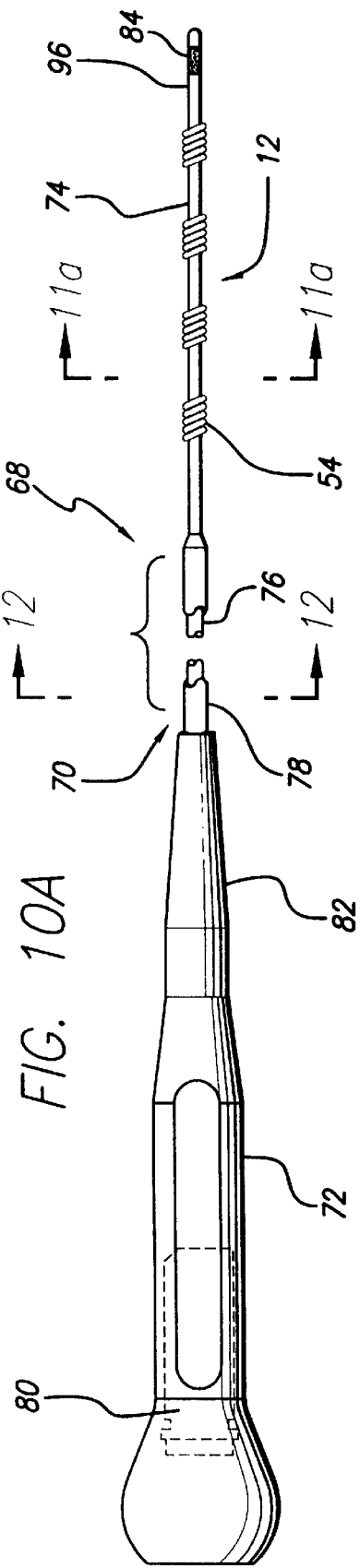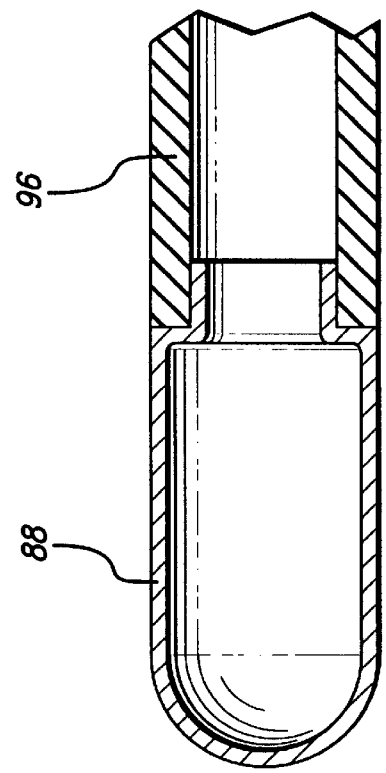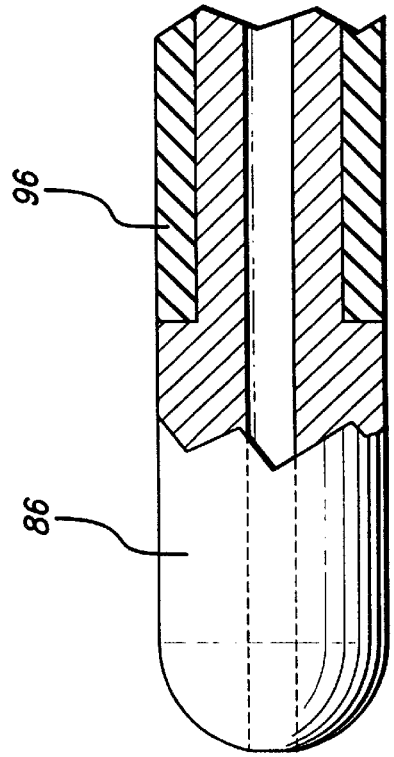

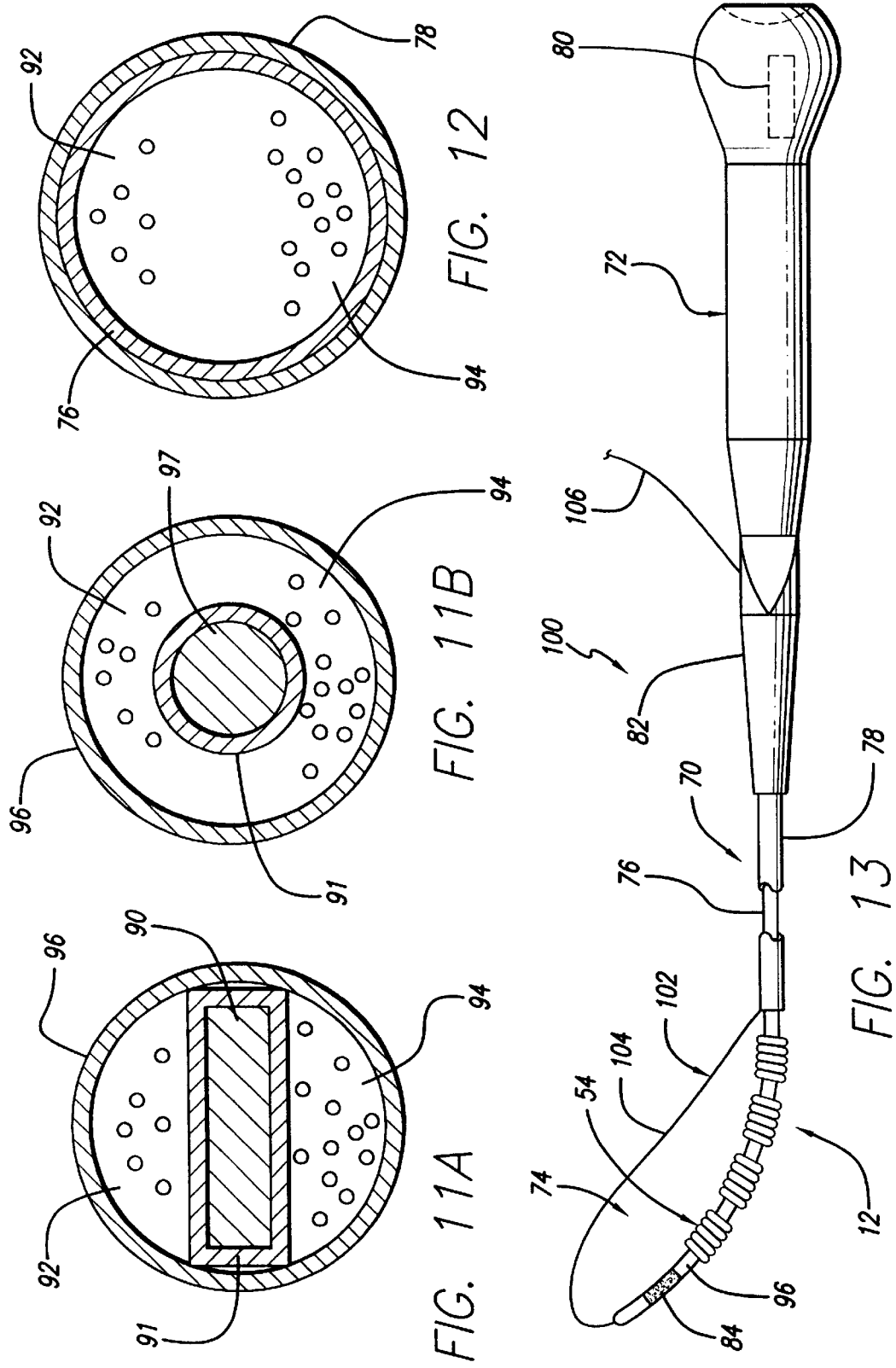

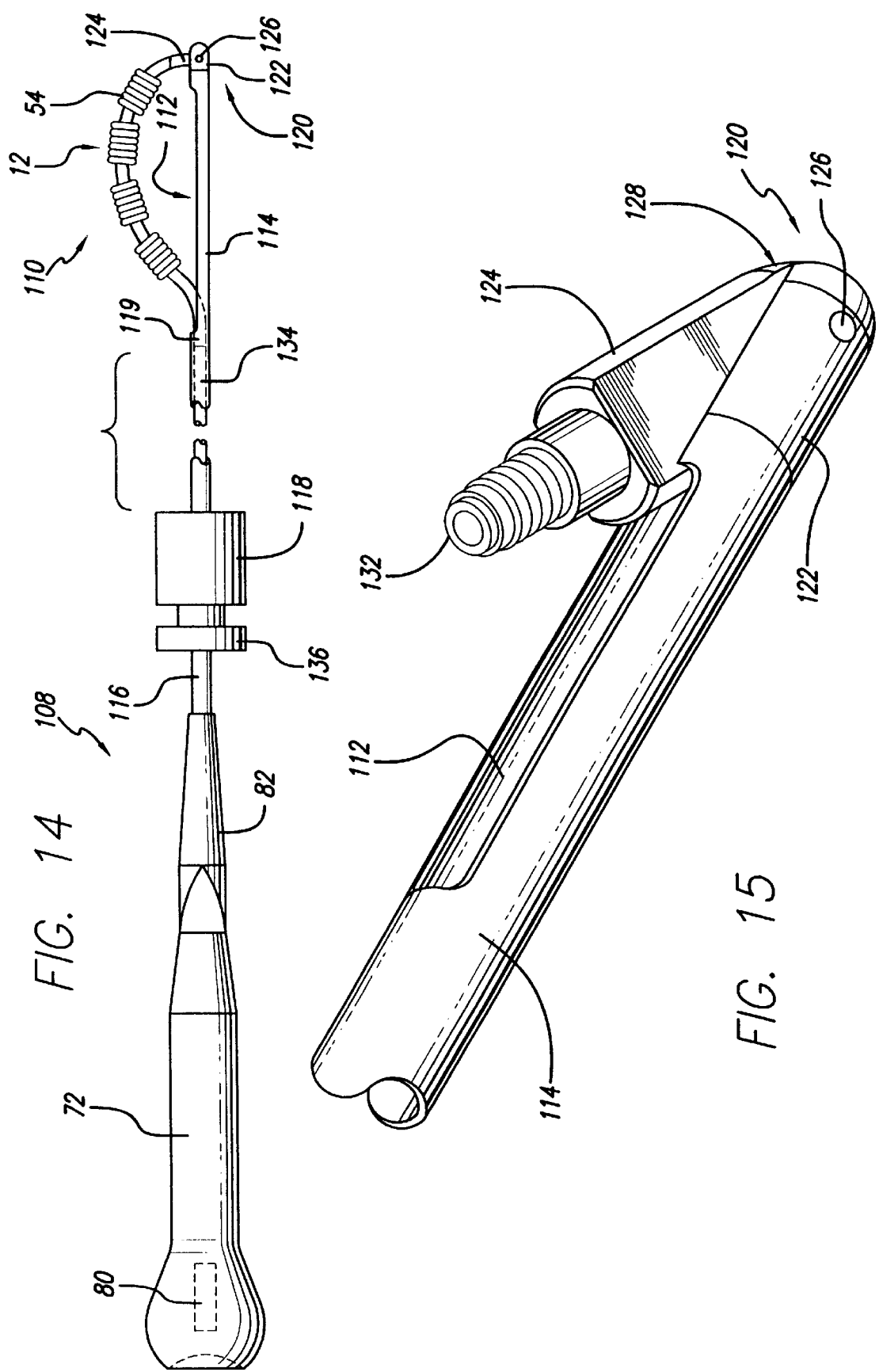

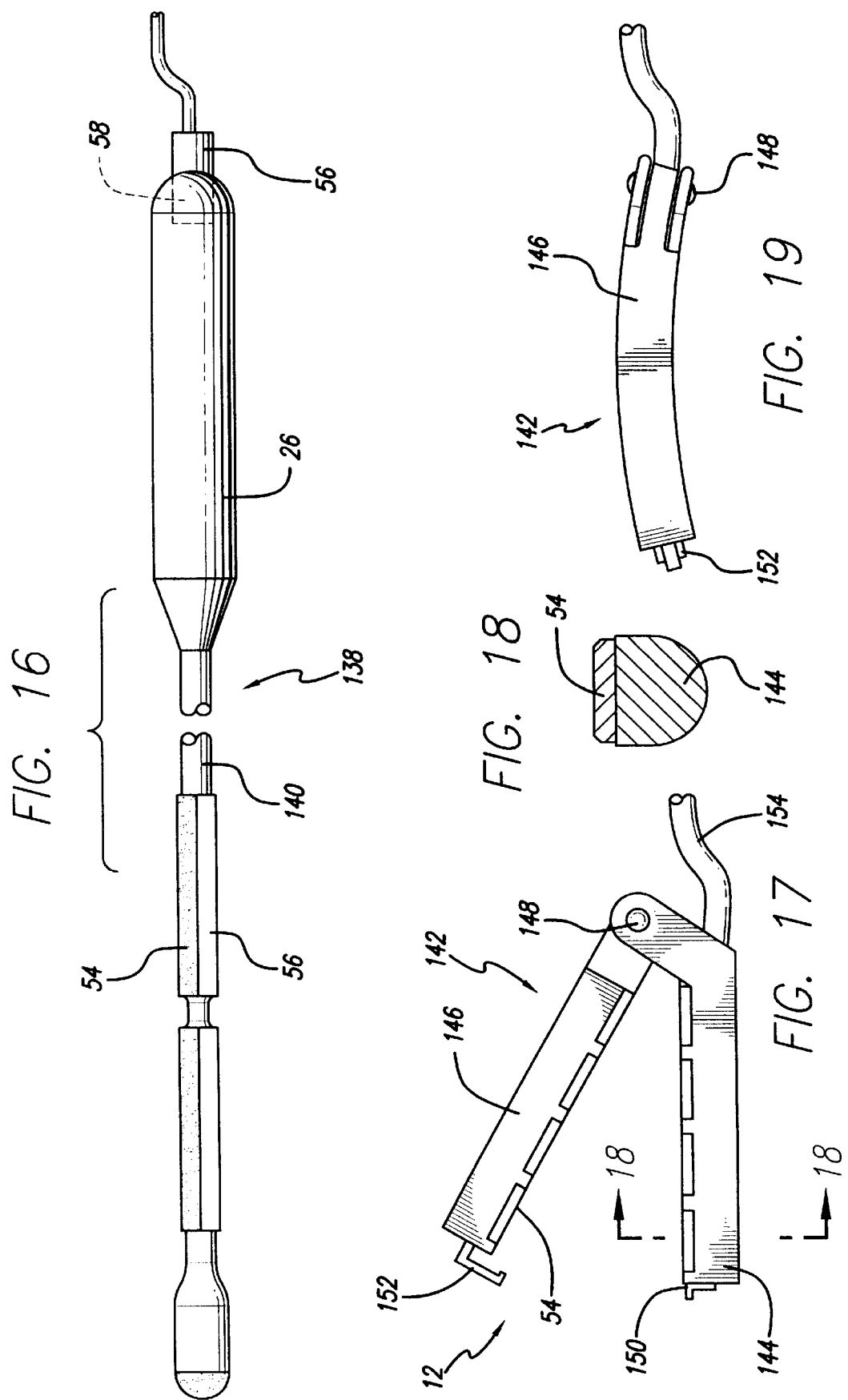

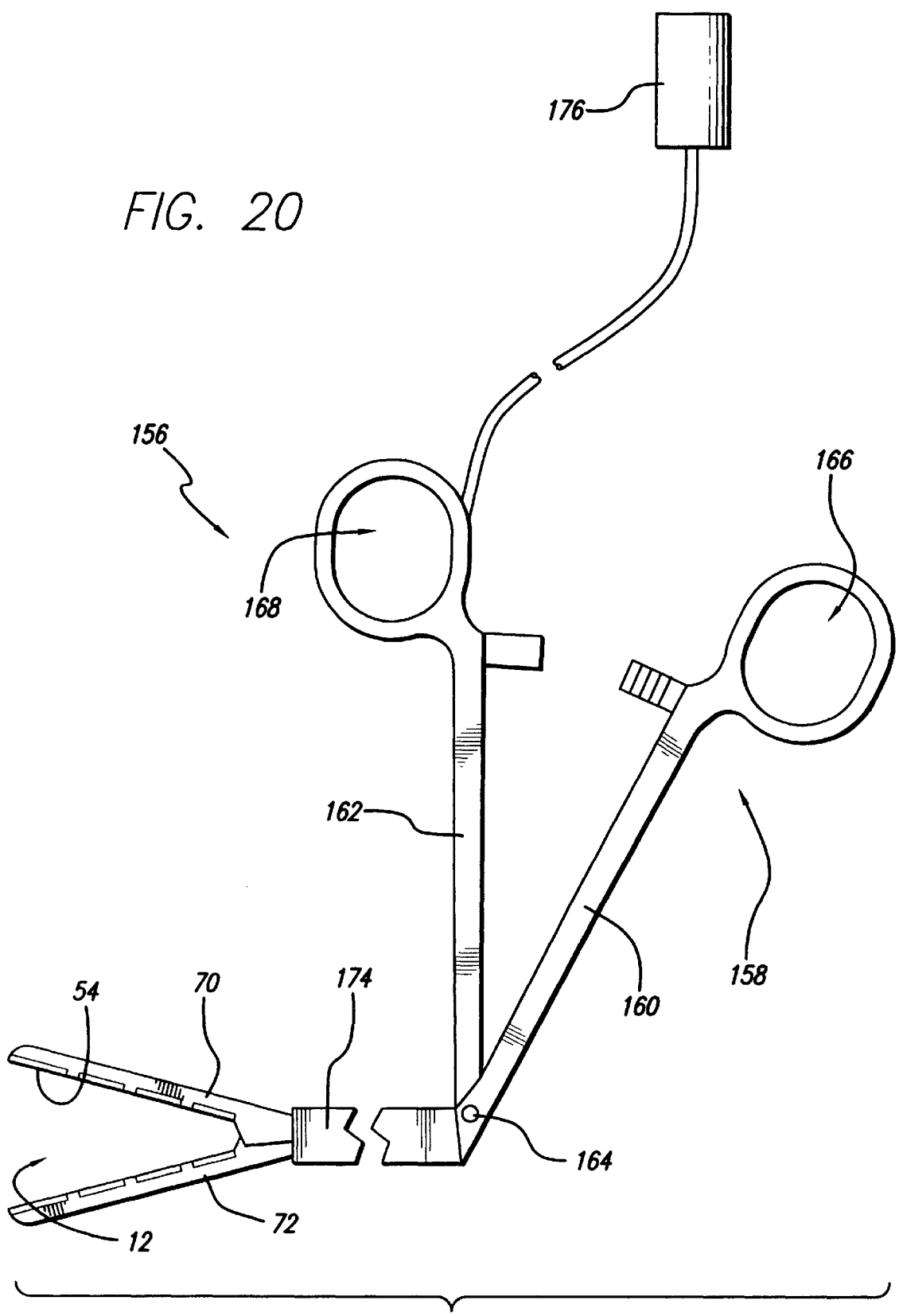

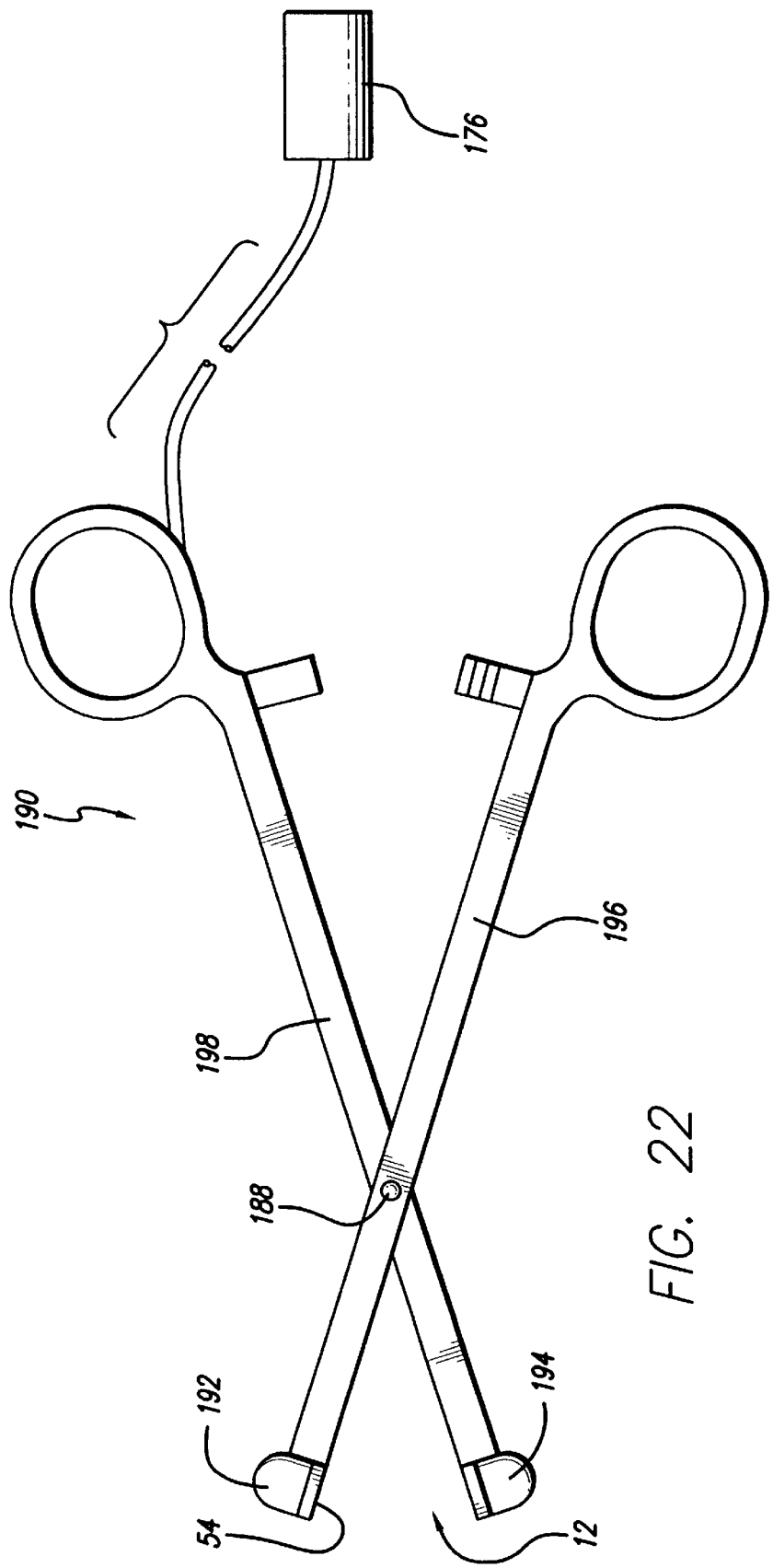

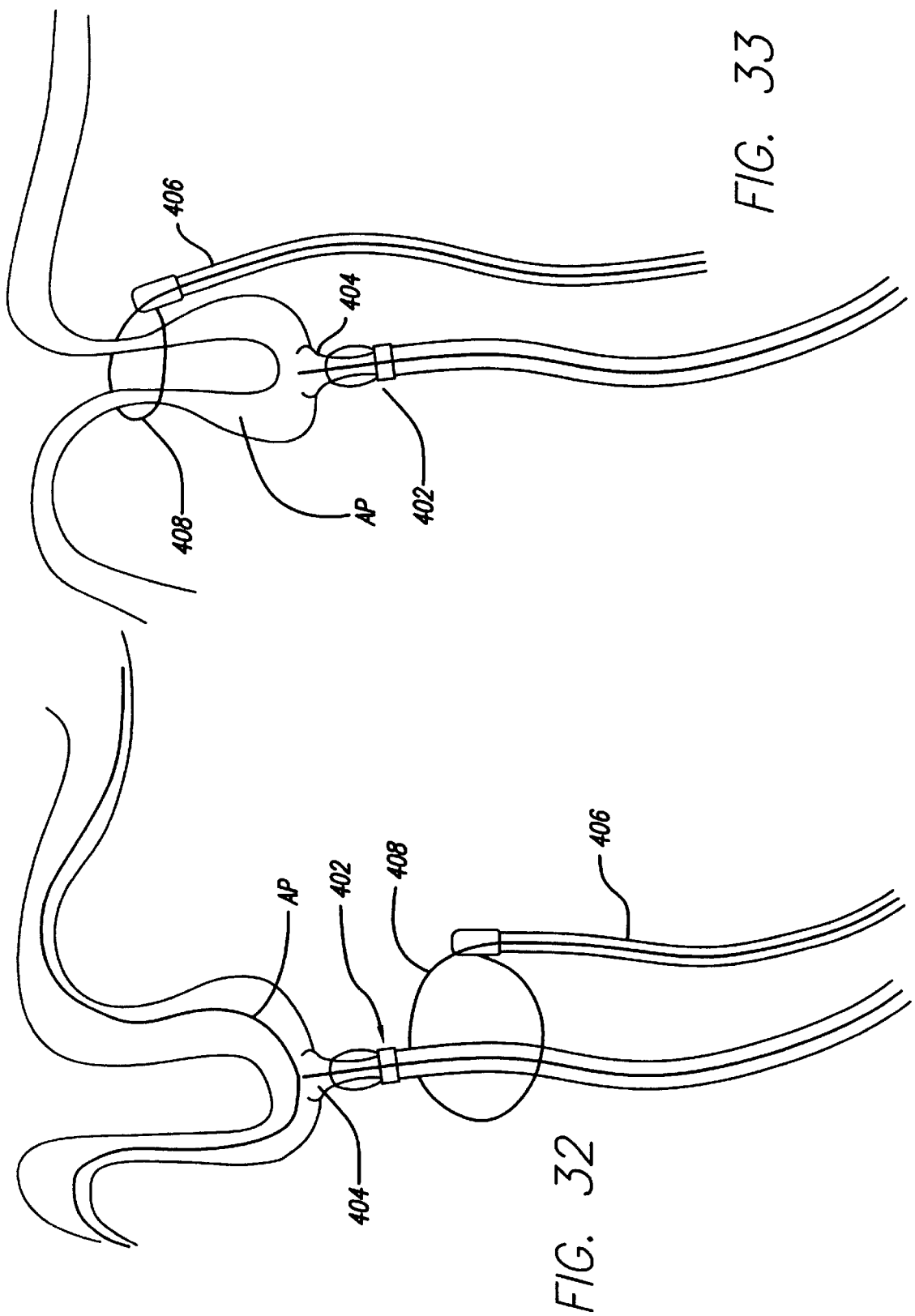

SURGICAL METHOD AND APPARATUS FOR POSITIONING A DIAGNOSTIC OR THERAPEUTIC ELEMENT WITHIN THE BODY

BACKGROUND OF THE INVENTION

1. Field of Invention

The present invention relates generally to structures for positioning one or more diagnostic or therapeutic elements within the body and, more particularly, to a device which is particularly well suited for treatment of cardiac conditions.

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

Although pharmacological treatment is available for atrial fibrillation and flutter, the treatment is far from perfect. For example, certain antiarrhythmic drugs, like quinidine and procainamide, can reduce both the incidence and the duration of atrial fibrillation episodes. Yet, these drugs often fail to maintain sinus rhythm in the patient. Cardioactive drugs, like digitalis, Beta blockers, and calcium channel blockers, can also be given to control the ventricular response. However, many people are intolerant to such drugs. Anticoagulant therapy also combats thromboembolic complications. Unfortunately, pharmacological remedies often do not remedy the subjective symptoms associated with an irregular heartbeat. They also do not restore cardiac hemodynamics to normal and remove the risk of thromboembolism.

Many believe that the only way to really treat all three detrimental results of atrial fibrillation and flutter is to actively interrupt all of the potential pathways for atrial reentry circuits.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery and is very expensive. Thus, despite its considerable clinical success, only a few maze procedures are done each year.

More recently, maze-like procedures have been developed utilizing catheters which can form lesions on the endocardium to effectively create a maze for electrical conduction in a predetermined path. Exemplary catheters are disclosed in commonly assigned U.S. Pat. No. 5,582,609. Catheters used to create lesions (the lesions being 3 to 15 cm in length) typically include a relatively long and relatively flexible body portion that has an ablation electrode on its distal end. The portion of the catheter body portion that is inserted into the patient is typically from 23 to 55 inches in length and there may be another 8 to 15 inches, including a handle, outside the patient. The proximal end of the catheter body is connected to the handle which includes steering controls. The length and flexibility of the catheter body allow the catheter to be inserted into a main vein or artery (typically the femoral artery), directed into the interior of the heart, and then manipulated such that the ablation electrode contacts the tissue that is to be ablated. Fluoroscopic imaging is used to provide the physician with a visual indication of the location of the catheter.

Atrial appendages are primary potential sources of thrombus formation. The atrial appendages are especially important in the transport of blood because they have a sack-like geometry with a neck potentially more narrow than the pouch. In this case, contraction of the appendage is essential to maintain an average absolute blood velocity high enough to eliminate potential stasis regions which may lead to thrombus formation.

In the maze procedure performed through open heart surgery, the typical access points into the interior of the atria are the atrial appendages. Therefore, at the conclusion of the surgical procedure, the region occupied by the atrial appendages is eliminated by surgically removing the appendages. This mitigates subsequent problems resulting from blood stasis in the atrial appendages as well as from electrical isolation of the appendages from the rest of the atria. However, as noted above, open heart surgery is very expensive and the incision based maze procedure is difficult to perform. Although catheter-based procedures do not admit themselves to surgical removal of the appendages, catheter-based procedures and apparatus have been recently developed which reposition the atrial appendages, affix them in an altered position and/or fuse the walls of the appendages to one another to isolate the appendages, reduce stasis regions and ultimately thrombus formation. Such procedures and apparatus are disclosed in commonly assigned U.S. application Ser. No. 08/480,200, filed Jun. 7, 1997, entitled "Atrial Appendage Stasis Reduction Procedures and Devices" and incorporated herein by reference. One of these procedures involves the use of a catheter having a lasso which is tightened around the appendage. Electromagnetic radio frequency ("RF") energy is then transmitted to the appendage by way of the lasso to thermally fuse the walls of the appendage to one another, thereby isolating the appendage.

Catheter-based ablation and atrial appendage isolation have proven to be a significant advance over the conventional open heart surgery based approaches. Nevertheless, the inventors herein have determined that further improvements are possible.

For example, and with respect to ablation procedures in particular, the inventors herein have determined that it can be quite difficult to accurately position an ablation electrode on the endocardium surface by manipulating the distal end of a relatively long catheter body from a remote handle. This is especially true with respect to left atrial sites. The present inventors have also determined that fluoroscopy is a somewhat inaccurate method of visualizing the ablation electrodes during positioning and when determining whether the electrodes are in proper contact with tissue.

Additionally, a primary goal of any ablation procedure is to create contiguous lesions (often long, curvilinear lesions) without over-heating tissue and causing coagulum and charring. Tissue ablation occurs at 50° C., while over-heating occurs at 100° C. The present inventors have further determined that it can be difficult to produce tissue contact that will accomplish this result with an electrode mounted on the distal end of a relatively long catheter. This is especially true in those procedures where an electrode on the distal tip of the catheter is dragged along the tissue. Such dragging also makes accurate placement of the electrode very difficult. Other shortcomings identified by the present inventors concern the convective cooling effects of the blood pool on the electrodes. For example, the system power requirements must be high enough to compensate for the heat losses due to convective cooling.

One proposed method of solving the over-heating problems associated with conventional ablation catheters is the so-called "cooled tip" approach. Here, the tissue surface is cooled with a saline solution. Although the saline is somewhat useful in keeping the surface temperature below the over-heating temperature, the sub-surface tissue temperature can still rise well above 100° C. Such temperatures will cause gas within the sub-surface tissue to expand. Ultimately, the tissue will tear or pop, which will result in perforations of the epicardial surface and/or the dislodging of chunks of tissue that can cause strokes.

Turning to atrial appendage isolation, the present inventors have determined that catheter-based procedures suffer from many of the same disadvantages discussed above, such as those concerning positioning and visualization. Additionally, the inventors herein have determined that the lasso can bunch up the tissue when the lasso is tightened and that tissue fusion would be improved if this bunching could be avoided.

SUMMARY OF THE INVENTION

Accordingly, the object of the present invention is to provide an apparatus for positioning an operative element (such as an ablation electrode) within the body which avoids, for practical purposes, the aforementioned problems.

In order to accomplish this and other objectives, a surgical device in accordance with one embodiment of the present invention includes a relatively short shaft, a bendable spline assembly associated with the distal end of the shaft and having a predetermined configuration, the spline assembly being adapted to collapse in response to external forces and expand when the forces are removed, and an operative element associated with the bendable spline. Optionally, a substantially tubular member may be positioned around the shaft. Movement of the substantially tubular member over the spline assembly will cause the spline assembly to collapse, while the spline assembly will expand to the predetermined configuration in response to a retraction of the substantially tubular member.

In order to accomplish this and other objectives, an ablation probe in accordance with another embodiment of the invention includes a relatively short shaft, a handle associated with the proximal end of the shaft, and ablation means for ablating tissue associated with the shaft and located in spaced relation to the handle.

In order to accomplish this and other objectives, a surgical device in accordance with another embodiment of the invention includes a relatively stiff shaft, a handle associated with the proximal end of the shaft, and a distal tip assembly associated with the distal end of the shaft, the distal tip assembly including a distal member, which is flexible and/or malleable, and an operative element carried by the distal member.

In order to accomplish this and other objectives, a surgical device in accordance with another embodiment of the invention includes a shaft, a relatively stiff tubular member positioned around a predetermined portion of the shaft and movable relative thereto, a distal tip assembly associated with the distal end of the shaft and including a flexible distal member and an operative element carried by the distal member, and a pivot assembly associated with the distal end of the tubular member and a distal portion of the tip assembly.

There are many advantages associated with these embodiments of the present invention. For example, these embodiments of the present invention may be used in a method of treating atrial fibrillation wherein access to the heart is obtained by way of a thoracostomy. Here, the operative element is an ablation electrode. Such a method may also be used to treat atrial fibrillation during mitral valve surgery wherein access to the heart is obtained through a thoracostomy, thoracotomy or median sternotomy.

The relatively short shaft and manner of insertion allows the ablation electrode to be easily inserted into the atrium and visually guided to the desired location. Thus, the ablation electrodes in the present device do not have to be guided by manipulating the relatively long shaft of an endovascular catheter. This makes the positioning of the electrodes within the heart easier and more accurate. Endocardial visualization is also improved because surgical methods employing the present device allow the endocardium to be viewed directly with the naked eye, a fiberoptic camera or other imaging modalities. This eliminates the need for fluoroscopic images and reduces the amount of radiation required, as compared to catheter-based procedures. Moreover, the shaft in the present device can be relatively stiff, as compared to a catheter shaft, because the present shaft does not have to travel through the tortuous vascular path to the heart. Along with the relatively short length of the present shaft, the additional stiffness enhances torque transmission and provides superior and more reliable electrode-endocardium contact force.

Surgical devices in accordance with the present invention may also be used during procedures, such as valve replacement where the patient is on cardiopulmonary bypass, to create tissue lesions. During bypass, the electrodes elements will not be in contact with the blood pool and, accordingly, will not be affected by the convective cooling.

Patients can only be on bypass for a period of approximately four hours. Long bypass times are associated with increased morbidity and mortality. Thus, all procedures performed during bypass must be rapidly completed. Surgical devices in accordance with the present invention may include a series of temperature controlled electrodes that allow a long lesion to be created in rapid fashion, i.e. in approximately 30 to 120 seconds. The ability of the present surgical devices and techniques to create lesions rapidly allows procedures to be performed during bypass that, heretofore, could not due to the time constraints. For example, a conventional surgical maze procedure takes approximately 12 hours to complete (note that a portion of the procedure is performed while the patient is not on bypass), while a such a procedure may be completed in approximately 5 to 15 minutes with the present devices and methods.

In accordance with another advantageous aspect of the present invention, the shaft and/or sheath (if present) may be formed from a malleable material that a physician can bend into a desired configuration and remain in that configuration when released. Although malleable, the stiffness of such material must be at least such that the shaft and/or sheath (if present) will not bend under the forces applied thereto during a surgical procedure. Alternatively, or in addition, the distal end of the device may also be malleable, thereby allowing the physician to bend the distal end of the device into a shape corresponding to the bodily structure to be acted upon. This is particularly important in endocardial applications because the endocardial surface is typically non-uniform with ridges and trabeculae residing in the right and left atria. There are also dramatic differences between in endocardial surface morphology from patient to patient and from lesion location to lesion location. To create contiguous lesions with a surgical approach, the device must either distend the atria to flatten out the non-uniformities, or the probe must be configured to conform to the atrial surface. There are, however, some regions where the atria cannot be distended to a flat state because of trabeculae, orifices, and ridges. A surgeon can observe the atrial surface and bend the present malleable device so as to conform thereto. The distal end may, instead, be spring-like or even rigid if the application so requires.

In order to accomplish the above-identified and other objectives, a surgical device in accordance with another embodiment of the present invention includes a handle having at least one movable handle member, first and second support members operably connected to the handle, at least one of the support members being movable with respect to the other support member in response to movement of the at least one movable handle member, and at least one ablation electrode associated with the first support member.

There are many advantages associated with this embodiment of the present invention. By way of example, this embodiment of the present invention is especially useful in a method of isolating an atrial appendage. Access to the atrium may be obtained by, for example, a thoracostomy and the appendage may be captured between the support members. RF energy is then applied to the captured portion of the appendage to thermally fuse the walls of the appendage to one another. This method provides better heating and fusing than the lasso catheter-based approach because the tissue is not bunched up when captured between the support members, as it is when the lasso is tightened. Additionally, the disadvantages associated with the use of catheters in general are also avoided.

A surgical clamp in accordance with another embodiment of the present invention includes first and second clamp members, and at least one electrode associated with at least one of the clamp members. The clamp may be used to isolate an atrial appendage in a manner similar to that described in the preceding paragraph with the same advantageous results. Thereafter, the clamp may be either removed or left in place.

The above described and many other features and attendant advantages of the present invention will become apparent as the invention becomes better understood by reference to the following detailed description when considered in conjunction with the accompanying drawings.

BRIEF DESCRIPTION OF THE DRAWINGS

Detailed description of preferred embodiments of the invention will be made with reference to the accompanying drawings.

FIG. 1 is a side, partial section view of a surgical device for positioning an operative element within a patient in accordance with a preferred embodiment of the present invention.

FIG. 2 is an end view of the surgical device shown in FIG. 1.

FIG. 3 is a side view of a surgical device for positioning an operative element within a patient in accordance with another preferred embodiment of the present invention.

FIG. 4 is a side, partial section view of a portion of the surgical device shown in FIG. 3.

FIG. 5 is a side view of a surgical device for positioning an operative element within a patient in accordance with still another preferred embodiment of the present invention.

FIG. 6a is a partial side, cutaway view of a surgical device for positioning an operative element within a patient in accordance with yet another preferred embodiment of the present invention.

FIG. 6b is a section view taken along line 6b—6b in FIG. 6a.

FIG. 7 is a section view showing an operative element coated with regenerated cellulose.

FIG. 8a is a section view showing a partially masked operative element.

FIG. 8b is a section view showing an alternative operative element configuration.

FIGS. 9a–9c are front views of a spline assembly in accordance with an embodiment of the present invention.

FIG. 9d is a side view of the spline assembly shown in FIGS. 9a–9c.

FIG. 9e is a section view taken along line 9e—9e in FIG. 9a.

FIG. 9f is a partial front, partial section view of a surgical device for positioning an operative element within a patient in accordance with yet another preferred embodiment of the present invention.

FIG. 10a is a side view of a surgical device for positioning an operative element within a patient in accordance with another preferred embodiment of the present invention.

FIG. 10b is a side, partial section view of an alternate tip that may be used in conjunction with the device shown in FIG. 10a.

FIG. 10c is a side, section view of another alternate tip that may be used in conjunction with the device shown in FIG. 10a.

FIG. 11a is a section view of the distal portion of the device shown in FIG. 10a taken along line 11a—11a in FIG. 10a.

FIG. 11b a section view of an alternate distal portion for the device shown in FIG. 10a.

FIG. 12 is a section view taken along line 12—12 in FIG. 10a.

FIG. 13 is a side view of a surgical device for positioning an operative element within a patient in accordance with still another preferred embodiment of the present invention.

FIG. 14 is a side view of a surgical device for positioning an operative element within a patient in accordance with yet another preferred embodiment of the present invention.

FIG. 15 is a perspective view of a portion of the device shown in FIG. 14.

FIG. 16 is a side view of a surgical device for positioning an operative element within a patient in accordance with still another preferred embodiment of the present invention.

FIG. 17 is a side view of a clamp in accordance with another preferred embodiment of the present invention.

FIG. 18 is a section view taken along line 18—18 in FIG. 17.

FIG. 19 is a top view of the clamp illustrated in FIG. 17.

FIG. 20 is a side view of a surgical device for positioning an operative element within a patient and applying a clamping force to a bodily structure in accordance with another preferred embodiment of the present invention.

FIG. 22 is a side view of a surgical device for positioning an operative element within a patient and applying a clamping force to a bodily structure in accordance with still another preferred embodiment of the present invention.

FIG. 32 is a fragmentary side view showing the use of a grabbing catheter in conjunction with a lasso catheter for maintaining the walls of the inverted appendage together.

FIG. 33 is a fragmentary view of the combination shown in FIG. 32 illustrating further steps of tying an appendage in an inverted orientation.

DETAILED DESCRIPTION OF THE PREFERRED EMBODIMENTS

Figure 21:
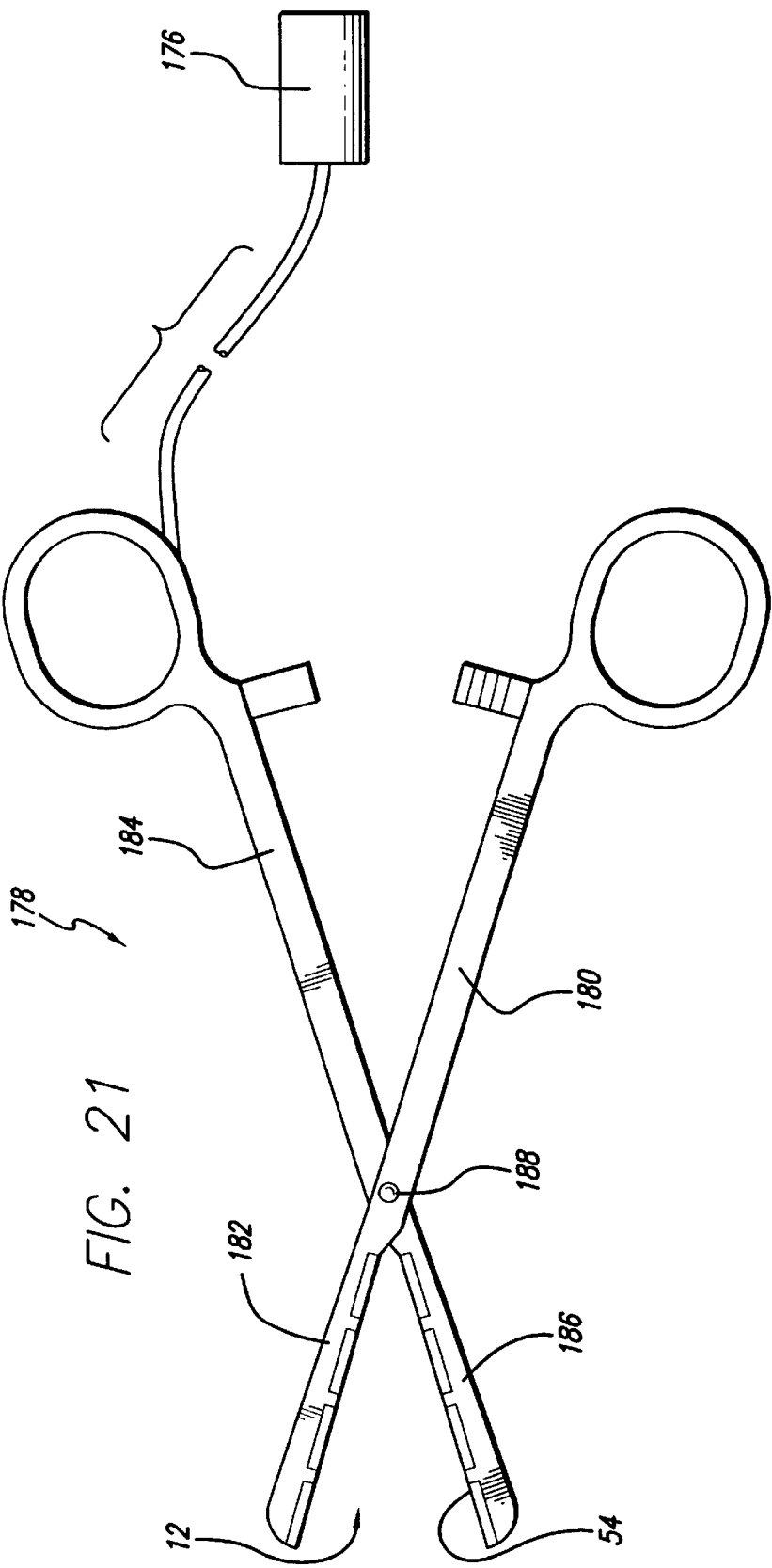
FIG. 21 is a side view of a surgical device for positioning an operative element within a patient and applying a clamping force to a bodily structure in accordance with another preferred embodiment of the present invention.

The following is a detailed description of the best presently known mode of carrying out the invention. This description is not to be taken in a limiting sense, but is made merely for the purpose of illustrating the general principles of the invention. The scope of the invention is defined solely by the appended claims.

The detailed description of the preferred embodiments is organized as follows:

I. Probe-Type Apparatus
II. Operative Elements
III. Epicardial Applications of Probe-Type Apparatus
IV. Endocardial Applications of Probe-Type Apparatus
V. Apparatus that Apply a Clamping Force
VI. Applications of Apparatus that Apply a Clamping Force
VII. Power Control The section titles and overall organization of the present detailed description are for the purpose of convenience only and are not intended to limit the present invention.

I. Probe-Type Apparatus

As illustrated for example in FIGS. 1 and 2, a surgical device (or "probe") 10 for positioning an operative element 12 within a patient includes a relatively short shaft 14 and a bendable spline assembly 16, associated with the distal end of the shaft, for supporting the operative element. Here, the operative element 12 is in the form of a plurality of electrode elements 54, as discussed in greater detail in Section II. Preferably, the relatively short shaft may be between approximately 4 and 18 inches in length, and is preferably 8 inches in long, while the outer diameter of the shaft is preferably between approximately 6 and 24 french. The spline assembly 16 has a predetermined use configuration. In the exemplary embodiment shown in FIGS. 1 and 2, the spline assembly includes a pair of spline legs 18 and 20 and an annular member 22 which supports the operative element 12. The surgical device also includes a tubular member 24 (a cylindrically shaped sheath in the exemplary embodiment) which covers a portion of the shaft 14 and is also slidable relative thereto. The spline assembly 16 is adapted to collapse (the insertion configuration) in response to movement of the substantially tubular member 24 in the distal direction and to expand to the predetermined use configuration when the substantially tubular member is moved in the proximal direction. A handle 26 may be provided on the proximal end of the shaft 14. The tubular member 24 preferably includes a raised gripping surface 28.

Another exemplary surgical device (or "probe") for positioning an operative element within a patient, which is generally represented by reference numeral 30, is illustrated in FIGS. 3 and 4. Here, the surgical device includes a substantially triangularly shaped spline assembly 32 that consists of first and second side legs 34 and 36 and a distal leg 38. The distal leg 38, which is preferably non-linear from end to end and approximately 10 to 12 cm in length, includes first and second linear portions 40 and 42 and a bent portion 44 located mid-way between the ends. This spline configuration provides a spring force against the selected bodily surface during use (such as the atrium wall in a cardiac procedure) and the bend in the distal leg 38 optimizes the contact between the operative element 12 and the selected surface. The spline assembly 32 will collapse in the manner shown in FIG. 4 when the tubular member 24 is advanced thereover and will return to the orientation shown in FIG. 3 when the tubular member is retracted. The surgical device 30 also includes a second handle 27.

During use of the exemplary surgical device shown in FIGS. 1–4, the handle 26 (FIG. 1) or 27 (FIG. 3) is grasped by the physician and force is applied through the shaft 14 and side legs 18 and 20 (FIG. 1) or 34 and 36 (FIG. 3) to the operative element supporting annular member 22 (FIG. 1) or distal leg 38 (FIG. 3). Thus, the shaft and side legs (including the area where the side legs meet) should be sufficiently strong to prevent collapse when the force is applied. The fact that the present devices are not passed through a tortured vascular path to the site of interest allows the shaft and spline legs to be stiffer than a conventional catheter shaft. This aspect of the invention is discussed in greater detail below. Alternatively, the shaft 14 and side legs 34 and 36 in the embodiment shown in FIGS. 3 and 4 may be configured such that they collapse and form a semicircle with the distal leg 38 when force is applied to the shaft. Here, the operative element should be appropriately masked in one of the manners described below to limit contact of the operative element to the intended bodily structure.

As shown by way of example in FIG. 5, a guidewire 46 may be used to direct and/or anchor the distal leg 38 of the exemplary spline assembly 32 in an anatomical anchor site (such as one of the pulmonary veins shown in FIG. 5). The guidewire 46 passes through a lumen in the shaft 14. The distal end of the guidewire 46 passes through a lumen 48 formed in one of the spline assembly side legs 34 and 36, while the proximal end is secured to a handle 50. Alternatively, two guide wires (one passing through each of the side legs) may be used to anchor the spline assembly 32 in two anatomical anchor sites. Both wires would extend to the same handle.

The exemplary embodiments illustrated in FIGS. 1–5 may also be provided without the tubular member 24. Such devices are especially useful in surgical procedures associated with a thoracotomy or a median sternotomy, where the spline assemblies can be easily collapsed and advanced to the desired location, or advanced into the desired location without being collapsed. Here, the spline assemblies can be malleable, if desired, as opposed to simply being bendable.

Turning to FIGS. 6a and 6b, an endoscope 52 may be passed through one lumen in a tubular member 24' that has a pair of lumens. Alternatively, the shaft 14 and endoscope 52 can pass through a common lumen.

The spline assemblies illustrated in FIGS. 1–5 are preferably made from resilient, inert wire, like nickel titanium (commercially available as Nitinol material) or 17-7 stainless steel. However, resilient injection molded inert plastic can also be used. The wire or molded plastic is covered by suitable biocompatible thermoplastic or elastomeric material such as PEBAX® or pellethane. Preferably, the various portions of the spline assemblies comprises a thin, rectilinear strips of resilient metal or plastic material. Still, other cross-sectional and longitudinal configurations can be used. For example, the spline legs can decrease in cross-sectional area in a distal direction, by varying, e.g., thickness or width or diameter (if round), to provide variable stiffness along its length. Variable stiffness can also be imparted by composition changes in materials or by different material processing techniques. Referring more specifically to the embodiments illustrated in FIGS. 3–5, the distal leg 38 may be configured such that the leg is flat at the distal end, but becomes more semicircular in cross-section as the leg becomes more proximal in order to taper the stiffness profile and prevent lateral movement of the spline assembly. The curvature of the spline legs may also be varied and the lateral ends of the distal leg may be reinforced in order to provide more lateral stability.

As shown by way of example in FIGS. 9a–9e, the spline assembly of the probe shown in FIGS. 3 and 4 may be replaced by a curved spline assembly 60. Here, the spline assembly includes a flat, inert wire 62 (preferably formed from Nitinol) that acts as a spring and an outer portion 64 (preferably formed from PEBAX® or pellethane). Viewed in cross-section, the flat wire 62 has a long side and a short side. The short sides lie in planes that are parallel to the plane shown in FIG. 9d. As such, the spline assembly 60 will deflect in the manner shown in FIGS. 9b and 9c when "in plane" forces F are applied to the spline assembly. Conversely, the assembly will resist bending when "out of plane" forces are applied in the manner shown in FIG. 9d. As such, it may be used to form an arcuate lesion during, for example, a procedure where a lesion is formed around the pulmonary vein.

It should be noted here that the wire 62 does not have to be rectangular in cross-section as shown. Other cross-sectional shapes where the length is greater than the width can also be used. The wire 62 can also be made from a malleable material such as partially or fully annealed stainless steel instead of the spring-like material discussed above. The malleable embodiments will enable the operator to form fit the ablation element support structure to irregular anatomical structures.

As shown in FIG. 9f, exemplary spline assembly 60' includes first and second steering wires 61a and 61b that are secured to the spring-like flat wire 62 by, for example, welding or adhesive bonding. The proximal ends of the steering wires 61a and 61b are operably connected to a knob 63 on a handle 26' by way of a cam (not shown). The handle 26' is substantially similar to the handle 26 shown in FIG. 1, but for the knob 63, cam and provisions for the steering wires 61a and 61b. Rotation of the knob 63 will cause the spline assembly to move side to side in, for example, the manner illustrated in FIG. 9c. Thus, in addition to simply moving the handle, the physician will be able to move the operative element 12 within the patient by rotating the knob 63. Such movement is useful when the physician is attempting to precisely locate the operative element within the patient and/or control the contact force between the operative element and the tissue surface. This is especially true when the handle and or shaft 14 cannot be moved, due to anatomical or surgical constraints.

In the exemplary embodiment, the steering wires 61a and 61b are both secured at about the midpoint of the flat wire loop. Other configurations are possible depending on the configuration of the loop that is desired after the knob 63 is rotated. For example, one wire could be secured closer to the top of the loop than the other. The shape of the cam may also be varied. More detailed discussions of the use of steering wires, albeit in conventional catheter settings, can be found in commonly assigned U.S. Pat. Nos. 5,195,968, 5,257,451, and 5,582,609, which are incorporated herein by reference.

The shaft 14 is preferably relatively stiff. As used herein the phrase "relatively stiff" means that the shaft (or other structural element) is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial. Rigid and somewhat flexible shafts are preferably formed from stainless steel, while malleable shafts are formed from annealed stainless steel.

One method of quantifying the flexibility of a shaft, be it shafts in accordance with the present invention or the shafts of conventional catheters, is to look at the deflection of the shaft when one end is fixed in cantilever fashion and a force normal to the longitudinal axis of the shaft is applied somewhere between the ends. Such deflection (σ) is expressed as follows:

$$\sigma = WX^2(3L-X)/6EI$$

where:

W is the force applied normal to the longitudinal axis of the shaft,

L is the length of the shaft,

X is the distance between the fixed end of the shaft and the applied force,

E is the modulous of elasticity, and

I is the moment of inertia of the shaft.

When the force is applied to the free end of the shaft, deflection can be expressed as follows:

$$\sigma = WL^{3/3}EI$$

Assuming that W and L are equal when comparing different shafts, the respective E and I values will determine how much the shafts will bend. In other words, the stiffness of a shaft is a function of the product of E and I. This product is referred to herein as the "bending modulus." E is a property of the material that forms the shaft, while I is a function of shaft geometry, wall thickness, etc. Therefore, a shaft formed from relatively soft material can have the same bending modulus as a shaft formed from relatively hard material, if the moment of inertia of the softer shaft is sufficiently greater than that of the harder shaft.

For example, a relatively stiff 2 inch shaft (either malleable or somewhat flexible) would have a bending modulus of at least approximately 1 lb.-in.² Preferably, a relatively stiff 2 inch shaft will have a bending modulus of between approximately 3 lb.-in.² and approximately 50 lb.-in.². By comparison, 2 inch piece of a conventional catheter shaft, which must be flexible enough to travel through veins, typically has bending modulus between approximately 0.1 lb.-in.² and approximately 0.3 lb.-in.². It should be noted that the bending modulus ranges discussed here are primarily associated with initial deflection. In other words, the bending modulus ranges are based on the amount of force, applied at and normal to the free of the longitudinal axis of the shaft, that is needed to produce 1 inch of deflection from an at rest (or no deflection) position.

As noted above, the deflection of a shaft depends on the composition of the shaft as well as its moment of inertia. The shaft could be made of elastic material, plastic material, elasto-plastic material or a combination thereof. By designing the shaft 14 to be relatively stiff (and preferably malleable), the surgical tool is better adapted to the constraints encountered during the surgical procedure. The force required to bend a relatively stiff 2 inch long shaft should be in the range of approximately 1.5 lbs. to approximately 12 lbs. By comparison, the force required to bend a 2 inch piece of conventional catheter shaft should be between approximately 0.2 lb. to 0.25 lb. Again, such force values concern the amount of force, applied at and normal to the free of the longitudinal axis of the shaft, that is needed to produce 1 inch of deflection from an at rest (or no deflection) position.

Ductile materials are preferable in many applications because such materials can deform plastically before failure due to fracturing. Materials are classified as either ductile or brittle, based upon the percentage of elongation when the fracture occurs. A material with more than 5 percent elongation prior to fracture is generally considered ductile, while a material with less than 5 percent elongation prior to fracture is generally considered brittle. Material ductility can be based on a comparison of the cross sectional area at fracture relative to the original cross area. This characteristic is not dependent on the elastic properties of the material.

Alternatively, the shaft could be a mechanical component similar to shielded (metal spiral wind jacket) conduit or flexible LocLine®, which is a linear set of interlocking ball and socket linkages that can have a center lumen. These would be hinge-like segmented sections linearly assembled to make the shaft.

The exemplary tubular member 24 illustrated in FIGS. 1–6b is preferably in the form of a relatively thin cylindrical sheath (e.g., with a wall thickness of about 0.005 inch) and has an outer diameter which is preferably less than 0.180 inch. The sheath material is preferably also lubricious, to reduce friction during movement of the sheath relative to the shaft 14 and spline assemblies 16 and 32. For example, materials made from polytetrafluoroethylene (PTFE) can be used for the sheath. The distal end of the sheath should be relatively flexible to prevent injury. If necessary, additional stiffness can be imparted to the remaining portion of the sheath by lining the sheath with a braided material coated with PEBAX® material (comprising polyethel block amide related to nylon). Other compositions made from PTFE braided with a stiff outer layer and other lubricious materials can be used.

Alternatively, the tubular member 24 may be relatively stiff and formed from the materials described above with respect to the shaft 14.

As shown by way of example in FIG. 10a, a surgical probe 68 in accordance with another embodiment of the present invention includes a relatively stiff shaft 70, a handle 72 and a distal section 74. The shaft 70 consists of a hypo-tube 76, which is either rigid or relatively stiff, and an outer polymer tubing 78 over the hypo-tube. A relatively stiff tube, either malleable or somewhat flexible, will preferably have a bending modulus of between approximately 3 lb.-in. and approximately 50 lb.-in.². The handle 72 is similar to the handle 26 discussed above in that it includes a PC board 80 for connecting the operative elements on the distal portion of the probe to a power source. The handle 72 preferably consists of two molded handle halves and is also provided with strain relief element 82. An operative element 12 (here, in the form of a plurality of electrode elements 54) is provided on the distal section 74. This embodiment is particularly useful because it can be easily inserted into the patient through an introducing port such as a trocar.

In those instances where a malleable shaft 70 is desired, the hypotube 76 may be the heat treated malleable hypo-tube 76 shown in FIGS. 10a, 12 and 13. By selectively heat treating certain portions of the hypo-tube, one section of the hypo-tube (preferably the distal section) can be made more malleable than the other. This will alleviate any discontinuity between the distal section 74 and the shaft 70 when the distal section is malleable.

A plurality of temperature sensing elements (such as theremocouples which are not shown) may be located on, under, abutting the edges of, or in between, the electrode elements 54 in any of the exemplary devices disclosed herein. Additionally, a reference temperature sensing element may be provided. For example, a reference temperature sensing 84 may provided on or near the distal tip of the device shown in FIG. 10a. The reference temperature sensor may, alternatively, be located in the handle so that room temperature will be used as the reference. Another alternative is to use an electronic circuit to function as the reference temperature sensor. A reference temperature sensor can also be placed on the patient or in the operating room and the physician can simply input the reference temperature into the power control device. It should be noted that the accuracy of the reference temperature sensor is less important in applications where the patient is on bypass because the convective cooling effects of blood flowing past the electrodes is substantially reduced. Also, the present surgical devices provide better tissue contact than conventional catheter-based devices, which provides more accurate temperature monitoring.

The distal section 74 can be either somewhat flexible, in that it will conform to a surface against which it is pressed and then spring back to its original shape when removed from the surface or, as noted above, malleable. A bending modulus of between 3 lb.-in.$^2$ and 50 lb.-in.$^2$ is preferred. As shown by way of example in FIG. 11a, a somewhat flexible distal section 74 may include a spring member 90, which is preferably either a solid flat wire spring (as shown) or a three leaf flat wire Nitinol spring, that is connected to the distal end of the hypo-tube 76. Other spring members, formed from materials such as 17-7 or carpenter's steel, may also be used. A series of lead wires 92 and 94 connect the electrode elements 54 and temperature sensor elements, respectively, to the PC board 80. The spring member 90 and leads wires 92 and 94 are enclosed in a flexible body 96, preferably formed from PEBAX® material, polyurethane, or other suitable materials. The spring member 90 may also be pre-stressed so that the distal tip is pre-bent in the manner shown in FIG. 10a. Also, an insulating sleeve 91 may be placed between the spring member 90 and the lead wires 92 and 94.

In those instances where a malleable distal portion 74 is desired, the spring member 90 may be replaced by a mandrel 97 made of suitably malleable material such as annealed stainless steel or beryllium copper, as illustrated for example in FIG. 11b. The mandrel will ideally be fixed to the distal tip of the device (by, for example, soldering, spot welding or adhesives) and run through the shaft into the handle where it will also be fixed to insure good torque transmission and stability of the distal tip. Alternatively, the malleable mandrel may be fixed directly within the distal end of the shaft's hypo-tube 76 and secured by, for example, soldering, spot welding or adhesives.

The distal portion 74 may also be formed by a hypo-tube that is simply a continuation of the shaft hypo-tube 76. However, the distal end hypo-tube can be a separate element connected to the shaft hypo-tube 76, if it is desired that the distal end hypo-tube have different stiffness (or bending) properties than the shaft hypo-tube.

The shaft 70 may be from 4 inches to 18 inches in length and is preferably 6 to 8 inches. The distal portion 74 may be from 1 inch to 10 inches in length and is preferably 2 to 3 inches. To facilitate the formation of long continuous lesions, the distal portion 74 preferably includes six spaced electrode elements 54 that are approximately 12 mm in length. The number and length of the electrode elements 54 can, of course, be varied to suit particular applications.

In accordance with some embodiments of the invention, and as shown by way of example in FIGS. 10b and 10c, the distal section 74 may be provided with a distal (or tip) electrode. Referring first to FIG. 10b, the distal electrode 86 may be a solid electrode with a through hole for one or more temperature sensors. Another exemplary electrode is the shell electrode 88 shown in FIG. 10c, which could also have one or more temperature sensors inside. The distal electrodes have a variety of applications. For example, a distal electrode may be dragged along an anatomical surface to create a long lesion. The distal electrode may also be used to touch up lesions (straight or curvilinear) created by electrode elements 54 if, for example, the distal section 74 does not exactly conform to the anatomical surface, and to continue lesions formed by the electrode elements. The distal electrode may also be used to create lesions in anatomical ridges that are shaped such that the integrity of the surgical device would be compromised if the distal section 74 were bent to conform to the ridge.

As shown by way of example in FIG. 13, an exemplary surgical probe 100 is provided with a pull wire 102 that allows the physician to adjust the curvature of the distal portion 74 from no curve, to a slight curve, an extreme curve, or even a loop, as desired. The pull wire distal portion 104 is connected to the distal tip of distal section 74. The distal portion of the pull wire enters the shaft proximal to the ablation electrodes, and the proximal portion 106 exits through an aperture formed in the handle 72. But for the pull wire 102, the probe 100 is substantially the same as the spring tip probe version shown in FIGS. 10a and 11a. Alternatively, the proximal portion of the pull wire 102 may be associated with a handle/knob arrangement such as that shown in FIG. 9f.

In accordance with another embodiment of the present invention, and as illustrated for example in FIGS. 14 and 15, a surgical probe 108 is provided with a distal loop structure 110 that includes an operative element 12 in the form of a plurality of electrodes 54. The distal loop structure 110, which extends through an opening 112 in a sheath 114, is connected to a shaft 116. The shaft is, in turn, connected to the handle 72. The proximal portion of the sheath 114 includes a handle 118 that allows the sheath to be moved distally and proximally. The stiffness of the loop structure 110 is less than that of the sheath 114. As such, when the sheath 114 is pulled in the proximal direction, the loop structure 110 will bulge out of the sheath opening 112 in the manner shown in FIG. 14. When the sheath 114 is returned to its distal most position, the loop structure 110 will slide back into the sheath such that the sheath and the loop structure are coaxial.

The exemplary loop structure 110 is similar to the distal portion 74 of the probe shown in FIGS. 10a and 11a in that it includes a spring member (not shown), such as a leaf spring or a flat wire spring (preferably formed from Nitinol), which is covered by a flexible material such as a PEBAX® tube 119. In addition to allowing the distal portion 110 to bulge outwardly, the spring member can be flat so that it also provides resilience which helps the distal portion conform to the anatomical surface of interest and prevents "out of plane bending."

In the exemplary embodiment illustrated in FIGS. 14 and 15, a pivot assembly 120 is provided on the distal end of the sheath 114. The pivot assembly 120 includes a base member 122 and a pivot member 124 which is secured to the base member by a pivot pin 126. Referring more specifically to FIG. 15, the pivot member 124 pivots within a slot 128 that is formed in the base member 122. The size and shape of the slot 130, and the location of the pivot member 124 therein, may be adjusted to adjust the shape of the loop. For example, the location of the pivot member 124 and the shape and size of the slot 130 may be varied such that the pivot member can only rotate 30, 60, 90 or 180°. However, up to 270° of rotation is possible. The pivot member 124 includes a connector 132 (such as the illustrated threaded connector) for securing the distal end of the loop structure 110 to the pivot member.

The rigidity, malleability, or flexibility of the probe 108 may be provided in a number of ways. For example, the sheath 114 may be formed from a rigid stainless steel hypo-tube, a relatively stiff somewhat flexible stainless steel hypotube, or a relatively stiff malleable annealed stainless steel hypo-tube. Additionally, or alternatively, the shaft 116 may be a rigid (or somewhat flexible) stainless steel hypo-tube or a malleable annealed stainless steel hypo-tube. In either case, the distal end 134 of the shaft 116 will abut the flexible portion of the loop structure 110. Other materials can, of course, be used in place of stainless steel. A rigid high durometer plastic tube, for example, may be substituted for the stainless steel hypo-tube in the sheath or shaft.

Once the sheath 114 and shaft 116 are positioned relative to one another such that the desired loop is produced, the sheath may be secured to the shaft by a touhy borst connector 136 that is secured to the distal end of the sheath 114 between the handle 118 and the handle 72.

An ablation probe 138 in accordance with another aspect of the present invention is illustrated, for example, in FIG. 16. The probe includes a shaft 140 (similar to shafts 14, 70 or 116 described above) on which one or more ablation electrodes 54 are mounted. As described in greater detail in Section II below, masking 56 may be used to control the focus of the ablation energy and/or prevent convective cooling when the probe is in the blood pool. A handle 26 is also provided. The shaft 140 is preferably between approximately 4 and 16 inches in length, between approximately 3 and 8 mm in diameter. Additionally, the shaft may either be rigid or relatively stiff and, if relatively stiff, can be either malleable or somewhat flexible. The ablation probe 138 may be used for a variety of procedures. For example, the shaft may be inserted into the heart to perform ablation procedures.

II. The Operative Elements

A. Exemplary Operative Elements

In the exemplary embodiments illustrated in FIGS. 1–16, the operative element 12 is made up of a plurality of electrode elements 54 which can serve a variety of different purposes. The operative elements may also be lumens for chemical ablation, laser arrays, ultrasonic transducers, microwave electrodes, and D.C. hot wires.

In the illustrated embodiments, the principal use of the electrode elements 54 is to transmit electrical energy and, more particularly, RF energy, to ablate heart tissue. However, the electrode elements 54 can also be used to sense electrical events in heart tissue. Alternatively, or in addition, the electrode elements 54 can serve to transmit electrical pulses to measure the impedance of heart tissue, to pace heart tissue, or to assess tissue contact. The electrode elements are preferably about 4 mm to about 20 mm in length.

The electrode elements 54 are electrically coupled to individual wires (see reference numeral 55 FIGS. 8b and 9e and reference numeral 92 in FIGS. 11a, 11b and 12) to conduct ablating energy to them. The wires are passed in conventional fashion through a lumen extending through one of the spline legs and the shaft 14 into a PC board in the handle 26, where they are electrically coupled to a connector 56 which is received in a port 58 (see FIG. 1). The connector 56 plugs into a source of RF ablation energy. A plurality of temperature sensing elements (not shown), such as theremocouples or thermistors, may also be provided on the spline assemblies shown herein. Such temperature sensing elements may be located on, under, abutting the edges of, or in between, the electrode elements 54. For temperature control purposes, signals from the temperature sensor elements are transmitted to the source of ablation energy by way of wires (see reference numeral 57 FIGS. 8b and 9e and reference numeral 94 in FIGS. 11a, 11b and 12) which are also connected to the PC board. Suitable temperature sensor elements and controllers which control power to an electrode based on a sensed temperature are disclosed in U.S. Pat. Nos. 5,456,682 and 5,582,609, which are incorporated herein by reference. The respective numbers of wires will, of course, depend on the numbers of sensors and electrodes used in a particular application. A suitable temperature control system is described below with reference to FIGS. 28–31.

The electrode elements 54 can be assembled in various ways. They can, for example, comprise multiple, generally rigid electrode elements arranged in a spaced apart, segmented relationship. The segmented electrodes can each comprise solid rings of conductive material, like platinum, which makes an interference fit about the annular spline member. Alternatively, the electrode segments can comprise a conductive material, like platinum-iridium or gold, coated upon the device using conventional coating techniques or an ion beam assisted deposition (IBAD) process. The electrodes can also be in the form of helical ribbons.

Alternatively, the electrode elements 54 can comprise spaced apart lengths of closely wound, spiral coils wrapped about the device to form an array of generally flexible electrode elements. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility.

Electrode elements 54 can be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks. As illustrated for example in FIG. 7, the electrode elements 54 can also include a porous material coating 59, which transmits ablation energy through an electrified ionic medium. For example, as disclosed in U.S. patent application Ser. No. 08/879,343, filed Jun. 20, 1997, entitled "Surface Coatings For Catheters, Direct Contacting Diagnostic and Therapeutic Devices," which is incorporated herein by reference, electrode elements and temperature sensor elements may be coated with regenerated cellulose, hydrogel or plastic having electrically conductive components. With respect to regenerated cellulose, the coating acts as a mechanical barrier between the surgical device components, such as electrodes, preventing ingress of blood cells, infectious agents, such as viruses and bacteria, and large biological molecules such as proteins, while providing electrical contact to the human body. The regenerated cellulose coating also acts as a biocompatible barrier between the device components and the human body, whereby the components can now be made from materials that are somewhat toxic (such as silver or copper).

For applications in which the ablation electrode is in contact with flowing blood as well as tissue, such as when the patient is not on bypass, coating electrodes with regenerated cellulose decreases the effect of convective cooling on the electrode because regenerated cellulose is a poor thermal conductor as compared to metal. Thus, the effect of convective cooling by blood flowing past the regenerated cellulose coated electrodes is diminished. This provides better control for a lesion-generating process because the hottest tissue temperature is closer to the ablation electrode.

Furthermore, the regenerated cellulose coating decreases the edge effects attributed to delivering RF energy to an electrode having a sharp transition between the conductive electrode and insulating material. The current density along the electrode and power density within tissue are more uniform, which reduces the incidence and severity of char and/or coagulum formation. The more uniform current density along the axis of the device also results in a more uniform temperature distribution at the electrode, which decreases the requirement for precise placements of the temperature sensors at the ablation electrodes. Additionally, by coating a device with regenerated cellulose to create the outer surface, less labor-intensive methods of forming electrodes and bonding wires to electrode surfaces can be used.

During the coating process, a device such as the one of the above-described distal spline assemblies is coated with a wet viscose solution. The viscose solution is preferably cellulose xanthate, which is a form of solubilized cellulose derivative that is dissolved in a sodium hydroxide solution. The viscose solution is dip-coated onto the distal end assembly, which includes the electrodes, signal wires, temperature sensors, etc. The coated device is then regenerated by contacting it with an acid, such as sulfuric acid, which converts the xanthate back into the cellulose structure. The term regenerated cellulose refers to cellulose which has been converted from a solubilized cellulose derivative back into a pure cellulose structure. This regeneration process creates large enough micro size pores in the coating allowing ionic transport yet small enough to prevent ingress of blood cells, infectious agents, such as viruses and bacteria, and large biological molecules such as proteins.

Once the cellulose is regenerated, it is rinsed with water to remove acid residuals and sulfur compounds. An oxidizing agent (bleach, etc.) may be added to the rinse water to accelerate the removal of sulfur compounds. After the cellulose is regenerated, it is fully cured in an environmental chamber at a low humidity. Thereafter, it is preferable to make the regenerated cellulose flexible when dry, and to do so moisture is reintroduced into the cellulose coating material by setting the environmental chamber to a higher humidity. Alternatively, a small quantity of a material such as glycerol may be applied to the coating, and the hydroscopic nature of the glycerol will hydrate the cellulose coating to create sufficient flexibility. An overall thickness range for operable regenerated cellulose coatings is from 0.001 inches to 0.015 inches, with a preferable thickness range being from 0.001 inches to 0.003 inches; a preferred thickness being approximately 0.002 inches.

Materials other than regenerated cellulose that are mechanically robust and that have suitable characteristics could be used for the coating material. Hydrophilic materials that have effective pore sizes from 500 to 500,000 Daltons with a porosity of 1–10% and which are biocompatible could be effective. Some types of hydrogels, such as those used for disposable contact lenses are good candidate materials. Plastic materials that have additives to make them semiconductive could also be used. The loaded plastic would need to have a resistivity in the range of about 200–2,000 ohm-cm, and would need to be applicable in very thin films to the device.

The thickness of the cellulose coating is controlled by the viscosity of the coating solution and the dipping rate, and a different viscosity of the coating solution can be achieved by diluting it with the sodium hydroxide solution. A variable wall thickness can be achieved by varying the extraction rate during the dipping process. The slower the extraction rate, the thinner the wall thickness, and the faster the extraction rate, the thicker the wall thickness. An increased coating wall thickness can also be obtained by multiple layers of coating. To ensure proper lamination between such layers, each layer is coagulated with a salt solution (sodium sulfate, etc.) before applying another layer. In addition, spraying and co-extruding the viscose solution over the electrodes and the distal section can also be used to achieve a variable wall thickness cellulose coating.

In another method for covering a distal electrode assembly, a tubular casing of regenerated cellulose material is created on a mandrel. The regenerated cellulose casing is then shrunk onto the distal assembly.

The regenerated cellulose coating may also be applied over a "wet" electrode element. The moisture from the wet electrode element prevents the electrode elements from sticking to tissue during an ablation procedure. A wet electrode element is formed by a material that has high absorption capacity for liquids, such as an open cell sponge, hydrogel or cloth. Alternatively, the regenerated cellulose coating may simply be wet prior to the procedure, such as an ablation procedure.

The electrode elements 54 may be operated in a uni-polar mode, in which the ablation energy emitted by the electrode elements is returned through an indifferent patch electrode (not shown) externally attached to the skin of the patient. Alternatively, the elements 54 may be operated in a bipolar mode, in which ablation energy emitted by one or more electrode elements is returned through other electrode elements. The amount of power required to ablate tissue ranges from 5 to 150 w.

B. Operative Element Considerations in a Bypass Environment

In the exemplary embodiments shown in FIGS. 1–6a, 7, 9a–f, 10, 13 and 14, the electrode elements 54 are exposed around their entire peripheries. These embodiments are particularly useful when the heart is on bypass and there is no blood flow within the heart. Here, air acts as an insulator and produces only modest convective cooling effects, as compared to a flowing blood pool that has a higher convection coefficient than virtually static air. Energy transmission is, therefore, essentially limited to the RF energy that is transmitted from the portion of the electrode surface that is in contact with the tissue to either a ground electrode, or another electrode within the group of electrode elements. The overall impedance of the system will increase (as compared to a situation where blood is present) due to the smaller effective surface area between the electrode and tissue.

Both of these conditions, focused RF energy and low heat dissipation into the air, will impact the ablation because they result in a high current density. When creating long lesions with a conventional catheter, char can be created as the tip is dragged because of the high current density and the difficulty in monitoring tissue temperature and controlling power that is inherent in the dragging process. The present invention, however, can take advantage of the high current density because the electrodes are not being dragged. For example, a number of electrodes can be used to ablate simultaneously because the effective (tissue contacting) surface area between all of the ablating electrodes is smaller and the convective cooling effects are reduced, as compared to situations where blood is present. This reduces the power requirements of the system. In addition, by using electrodes with lower thermal mass (as compared to a conventional solid tip electrode), less heat will be retained by the electrode and better temperature sensing can be made at the tissue surface. This will speed up the creation of the lesions and enable better lesion creation control.

It is also noteworthy that the masking described in the following section can be useful during bypass because tissue can partially wrap around the electrodes when the distal end of the device is pressed against the tissue. Such masking can also be used to control lesion thickness.

C. Operative Element Considerations in a Non-Bypass Environment

In instances where the patient will not be on bypass and blood will be flowing past the electrodes, the portion of the electrode elements (or other operative elements) not intended to contact tissue may be masked through a variety of techniques. For example, a layer of UV adhesive (or another adhesive) may be painted on preselected portions of the electrode elements to insulate the portions of the elements not intended to contact tissue. Alternatively, a slotted sheath may be positioned over the portion of the electrode elements not intended to contact tissue. Deposition techniques may also be implemented to position a conductive surface only on those portions of the spline assembly intended to contact tissue.

As shown by way of example in FIG. 8a, a polymer layer 56 may be thermally fused over the electrodes 54 to mask desired portions of the electrodes. An exemplary process for applying the polymer layer is as follows. A segment of shaft tubing is cut long enough to cover the desired electrodes, and is then split in half (or other desired angle) along the axis. One half is placed over the assembled distal section so that it covers the side of the electrodes that are to be masked. A piece of polymeric shrink tubing, preferably RNF-100 or irradiated LDPE, is then carefully slid over the catheter distal end, so that the mask tubing is not moved from its placement over the electrodes and so that it stops approximately 2 cm beyond the end of the tubing half. The distal end is then heated in a controlled heat source at approximately 400° F. so that the mask tubing fuses into the distal shaft tubing along its length, and so that all of its edges are well fused into the shaft tubing, but not fused so much that the covered electrodes begin to poke through. Finally, the polymeric shrink tubing is split on one end and the assembly is heated at approximately 225° F. while the polymeric shrink tubing is slowly peeled off of the fused catheter shaft.

Additionally, as illustrated in FIG. 8b, the shape of an electrode 54' may be such that the metallic material in the region not intended to contact tissue is eliminated.

The masking techniques described in the preceding paragraph improve the efficiency of, for example, an ablation procedure by decreasing the surface area of the electrodes and, therefore, the energy required to heat tissue. The masking can be used to form a narrow electrode which is sometimes desirable, even when the patient will be on bypass. The convective cooling effects of blood flowing by the electrode are also reduced. In addition, the transmission of RF energy to unintended anatomic structures is prevented. This is especially important in epicardial applications when the ablation electrode elements may be sandwiched between multiple anatomic structures including, for example, the aorta and pulmonary artery.

III. Epicardial Applications of Probe-Type Apparatus

The exemplary surgical devices described above (primarily those discussed above with reference to FIGS. 10a–16) may be used in a variety of epicardial procedures. One such procedure is a maze-like ablation procedure to prevent atrial fibrillation. A thoracostomy, which is a surgical procedure that is less invasive than a thoracotomy or median sternotomy, may be used to gain access to the atrium. Here, relatively small incisions are created in the intercostal space. At each of the incisions, a trocar may be used to provide a port to access the thoracic cavity. These ports may be used for visualization with fiberoptic cameras, ultrasound, or other visualization devices, as well as for the surgical devices that ablate tissue. The surgical devices may be, for example, inserted through the ports located on the left side of the patient which provide direct access to the left atrium. The devices may then be used to create long, thin, curvilinear lesions or annular lesions on the epicardial surface. If necessary, lung lobes may be deflated during the procedure by inserting an endotracheal tube that inflates the right lung only. The left lung will collapse when the chest is opened.

There is also a high prevalence of atrial fibrillation substrates proximate to the pulmonary veins. Lesions may be created on the epicardial surface around pulmonary veins or between pulmonary veins. There is, however, some difficulty associated with epicardial access due to the presence of fatty deposits in the pulmonary vein region. The devices described above can create lesions on the epicardial surface proximate to the pulmonary veins because they can penetrate through fatty deposits and exert enough force against the epicardial surface to compress the remaining fat to such an extent that the ablation electrodes contact the epicardium. It is, however, very difficult to achieve suitable contact between the tissue and the electrodes. Thus, it is preferable to perform endocardial ablation around or between pulmonary veins in the manner described below.

IV. Endocardial Applications of Probe-Type Apparatus

The exemplary surgical devices described above with reference to FIGS. 1–16 may be used in a variety of endocardial procedures. To create lesions on the endocardial surface, access to the interior of the left atrium must also be obtained. To obtain thoracoscopic access to the left atrium via a thoracostomy, a cannula may be inserted through the left atrial appendage or the left atrial free wall. The preferred access point is the left atrial appendage, especially if the physician intends to isolate the left atrial appendage at the end of the procedure. More specifically, and as shown by way of example in FIGS. 32 and 33, a grabbing catheter 402 having movable grasping prongs 404, which is described in U.S. application Ser. No. 08/480,200, may be used to capture, pull and stretch the appendage AP. Next, a lasso catheter 406 having a lasso 408, which is also described in U.S. application Ser. No. 08/480,200, may be used to encircle the left atrial appendage near the base of the appendage. The grabbing catheter facilitates the positioning of the lasso at the base of the appendage by pulling the appendage through the lasso. A needle is then used to puncture the appendage wall and gain access to the left atrium. A guidewire is advanced through the needle into the left atrium. The needle is then removed, leaving the guidewire in place. An introducer/dilator combination is then advanced over the guidewire into the left atrium. Next, the lasso is then tightened around the introducer to prevent blood flow past the introducer into the distal region of the atrial appendage. The dilator is then removed, leaving the introducer as the access to the interior of the left atrium.

Instead of the lasso technique, a purse string technique may be employed wherein sutures are used to tighten the atrial appendage around the introducer.

One of the exemplary surgical devices described above with reference to FIGS. 1–9f may then be inserted into the atrium with its spline collapsed. Once inside, the sheath is retracted such that the spline returns to its predetermined configuration and the ablation procedure is performed. The sheath is pushed over the spline when the ablation procedure is complete and the device is removed from the atrium. Similarly, the devices described above with reference to FIGS. 14–15 may be inserted with the loop in its retracted state, while the device shown in FIG. 13 may be inserted prior to pulling the wire attached to the distal tip. These devices may then be manipulated to cause the loops to form. The ablation procedure can then be performed. The devices described above with reference to FIGS. 10a–c, 12 and 16 need only be inserted to perform the procedure. The same is also true for malleable versions of the exemplary devices shown in FIGS. 1–9e.

Upon completion, the introducer is removed and the lasso tightened to isolate the left atrial appendage. The lasso may be detached from the probe and left in place to keep the appendage isolated. Where the aforementioned purse string technique is employed, the sutures may be tightened isolate the appendage. Alternatively, the appendage may be isolated in the manner described below with reference to FIG. 26.

In addition to thoracoscopic procedures, another area of cardiac treatment which will benefit from the present invention is the repair and replacement of mitral valves (which typically involves a thoracotomy, median sternotomy, or thoracostomy) because atrial fibrillation can be a complication of mitral disease which occurs prior to or subsequent to mitral valve surgery. More specifically, incisional reentry can develop subsequent to surgical procedures (such as mitral valve and thoracoscopic procedures) where an incision is made in the atrial wall that is subsequently closed by either sutures, mechanical closures, or other similar devices. Creating a lesion from the incision to the mitral valve annulus (or other anatomic barrier) will reduce the potential for reentrant propagation around the incision and, therefore, will terminate atrial fibrillation and/or prevent atrial fibrillation from developing. For example, if the left atrial appendage is used to access the interior of the left atrium for devices that create lesions on the endocardial surface, an additional lesion should be created from this access site to the mitral valve annulus so that incisional reentry will not develop when the incision is closed. This additional procedure is also applicable for right atrial procedures using incisions to access the interior of the atrium.

There is also a high prevalence of atrial fibrillation substrates proximate to the pulmonary veins. The creation of long, curvilinear lesions between pulmonary veins, around single pulmonary veins, and/or from pulmonary veins to the mitral valve annulus will prevent atrial fibrillation. The exemplary device illustrated FIGS. 1 and 2, which has an annular electrode assembly, is especially well suited for positioning ablation electrodes around the inside of a pulmonary vein. Alternatively, lesions may be created on the epicardial surface around pulmonary veins or between pulmonary veins. There is, however, some difficulty associated with epicardial access due to the presence of fatty deposits in the pulmonary vein region.

V. Apparatus that Apply a Clamping Force

In accordance with another aspect of the present invention, and as shown by way of example in FIGS. 17–19, a clamp 142 includes a pair of clamp members 144 and 146, which are pivotably secured to one another by a pin 148, and an operative element 12 that may be of the type discussed above in Section II. Here, the operative element consists of a plurality of ablation electrodes 54. The clamp 142 also includes a pair of locking members 150 and 152 and an electrical connector 154 that may be used to, for example, connect the electrodes 54 to a source RF energy. Referring more specifically to FIG. 19, the clamp 142 may also, if desired, be curved over its length. Of course, the overall shape of the clamp will depend upon the procedure for which it is intended.

Certain procedures require the application of a clamping force to the bodily structure of interest in addition to the operation performed by the operative element. One such procedure is the isolation of an atrial appendage, which is discussed in greater detail below with reference to FIG. 26. As illustrated for example in FIG. 20, a suitable surgical device 156 for use in such a procedure includes a handle 158 having a pair of handle members 160 and 162 which are movable relative to one another. In the exemplary embodiment, the handle members are pivotably secured to one another by a pin 164 and include respective openings 166 and 168. The handle 158, which is actuated in a manner similar to scissors, is operably connected to a pair of support members 170 and 172 by, for example, a suitable mechanical linkage located within a housing 174. Actuation of the handle 158 causes the support members 170 and 172 to move relative to one another to create a clamping force. Of course, other types of handles that can cause movement of the support members may also be used.

An operative element 12, is associated with one or both (as shown) of the support members 170 and 172. Preferably, the operative element consists of one or more electrode elements 54 suitable for ablation (such as those discussed in detail in Section II above and operable in either the uni-polar or bi-polar mode) on each of the support members 170 and 172. Of course, the operative element 12 may also consist in whole or in part of other types of electrodes, such as a hot tip to cauterize appendage walls. The electrode elements 54 (or other operative element) may be connected to a control/power source surgical device by way of a connector 176. Wires extend from the electrode elements 54 through lumens in the support members 170 and 172 and handle 158 to the connector 176.

Turning to FIG. 21, surgical device 178 is similar to that shown in FIG. 20 except that handle 158 is not connected to the operative element support members 170 and 172 by a mechanical linkage. Instead, the handle member 180 and support member 182 form an integral unit as do the handle member 184 and support member 186. The integral units are pivotably secured to one another by a pin 188. Thus, while the embodiment shown in FIG. 20 is especially useful in situations where thoracostomy is used, the embodiment shown in FIG. 21 is especially useful for thoracotomy or median sternotomy access. In either case, the atrial appendage (or other bodily structure) is captured (or clamped) such that it is perpendicular to the surgical device.

Figure 23:
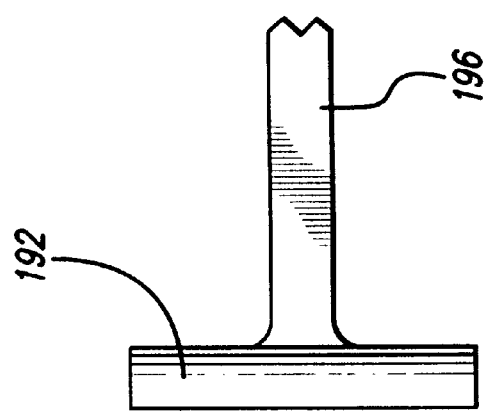
FIG. 23 is a top view of the operative element supporting member of the surgical device shown in FIG. 22.

As shown by way of example in FIGS. 22 and 23, the operative element support members 192 and 194 in exemplary surgical device 190 are secured to the distal ends of the handle members 196 and 198, respectively, such that the support members are perpendicular to the handle members. Although the handle members 196 and 198 are respectively secured to the middle portion of the support members 192 and 194 (viewed longitudinally as shown in FIG. 23), the support members may be offset in one direction or the other to suit particular needs. Additionally, as illustrated for example in FIG. 24, the support members may also be curved. The preferred embodiments shown in FIGS. 22–24 hold the bodily structure such that it is parallel to the surgical device.

Figure 24:
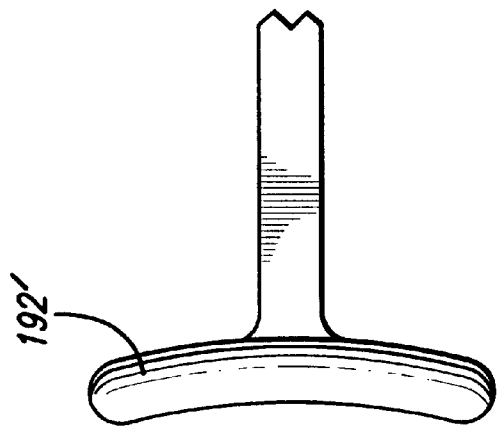
FIG. 24 is a top view of another operative element supporting member.
Figure 25:
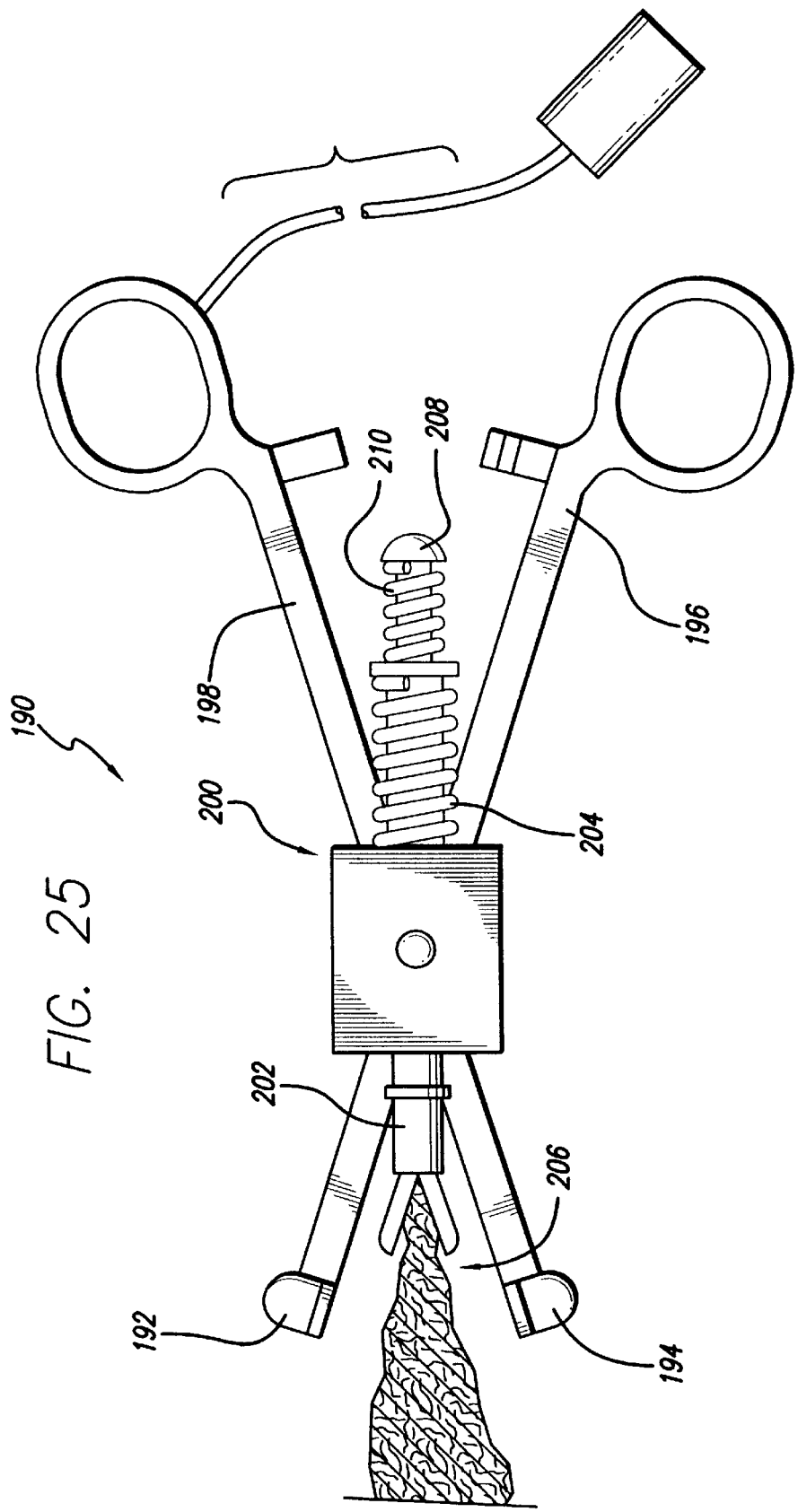
FIG. 25 is a side view of a surgical device for positioning an operative element within a patient and applying a clamping force to a bodily structure in accordance with yet another preferred embodiment of the present invention.

The exemplary embodiments shown in FIGS. 22–24 may be provided with a holding device that is used to grasp a bodily structure and pull the structure in the proximal direction. As illustrated for example in FIG. 25, the holding device 200 includes a cylindrical member 202 that is biased in the proximal direction by a spring 204. A pair of clamping jaws 206 extend outwardly from the distal end of the cylindrical member 202. The clamping jaws 206, which pivot relative to one another, are connected to a rod 208 which passes through the cylindrical member 202 and slides relative thereto. The rod 208 is biased in the proximal direction by a spring 210 which, in turn, biases the clamping jaws 206 in the proximal direction against the distal end of the cylindrical member 202. As such, the clamping jaws 206 are biased to their closed position and the jaws may be loosened by pushing the rod 208 in the distal direction.

VI. Applications of Apparatus that Apply a Clamping Force

The exemplary clamp 142 shown in FIGS. 17–19 can both isolate a bodily structure and deliver the therapeutic and/or diagnostic effects of the operative element 12. In an atrial appendage isolation procedure, for example, the clamp 142 may be used to capture the atrial appendage and isolate it from the interior of the atrium. RF energy may then be delivered via the electrodes 54 (in either the uni-polar mode or the bi-polar mode) to fuse the walls of the atrial appendage to one another. Thereafter, the clamp may either be removed, or disconnected from the RF energy source and left in place.

Figure 26:
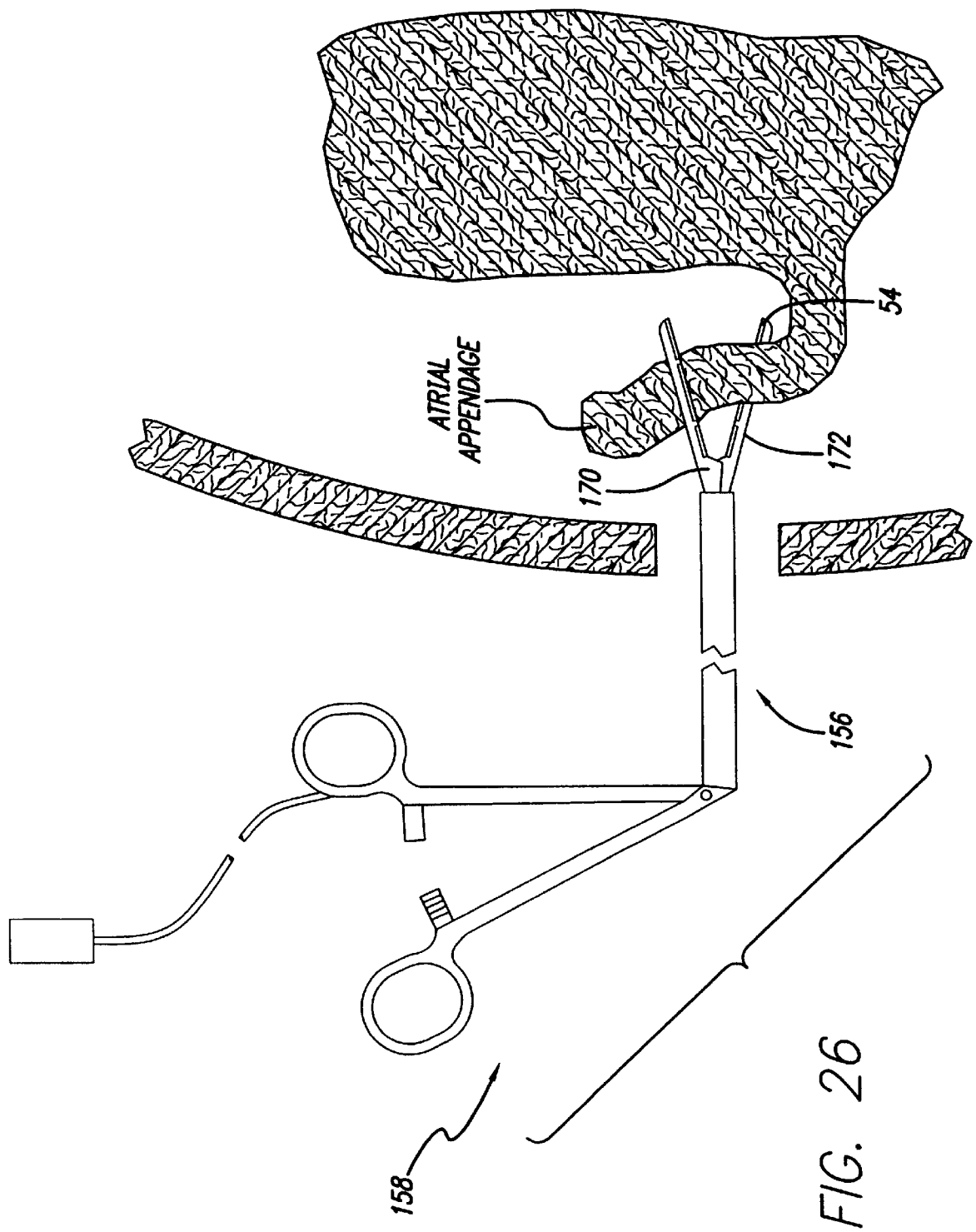
FIG. 26 is a side, partial section view of an exemplary procedure involving the surgical device shown in FIG. 20.

Turning to FIG. 26, one exemplary use of the surgical device 156 shown in FIG. 20 is the isolation of an atrial appendage. Here, the device in inserted into an opening of the chest wall. The atrial appendage is captured between the support members 170 and 172 by actuating the handle 158. RF energy is then transmitted, either from the electrodes 54 on one support member to the electrodes on the other (bi-polar mode) or from the electrodes to an indifferent reference electrode on, for example, a patch (uni-polar mode) to thermally fuse the walls of the atrial appendage together and isolate the atrial appendage. The surgical device shown in FIGS. 21–25 may be used in similar fashion.

Figure 27:
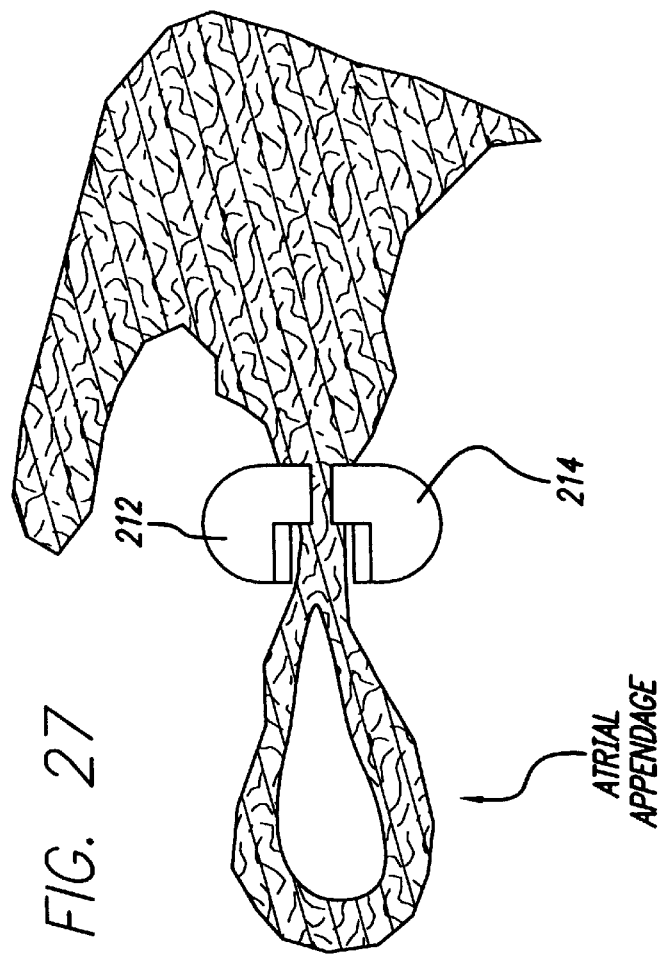
FIG. 27 is a side, partial section view of an exemplary procedure involving a surgical device having an alternate support member configuration.

As shown by way of example in FIG. 27, the operative element (such as, for example, electrodes 54) may be offset from one side or the other of the support members 212 and 214. This offset configuration, which may be used in conjunction with any of the exemplary devices shown in FIGS. 20–25, is especially useful in an atrial appendage isolation procedure. Here, the electrodes 54 are offset from the side of the support members 212 and 214 that is proximate to the interior of the left atrium. By making the portions of the support members that do not support the electrodes insulative, and by directing the RF energy towards the side of the appendage (or other structure) isolated by the clamping force, coagulum or thrombus due to heating static blood will develop in the portion of the appendage that will be isolated from the blood pool when the side walls fuse to one another. Of course, when the patient is in bypass, such masking is unnecessary unless it is being used to create lesions of a certain shape.

VII. Power Control

A. General

Figure 28:
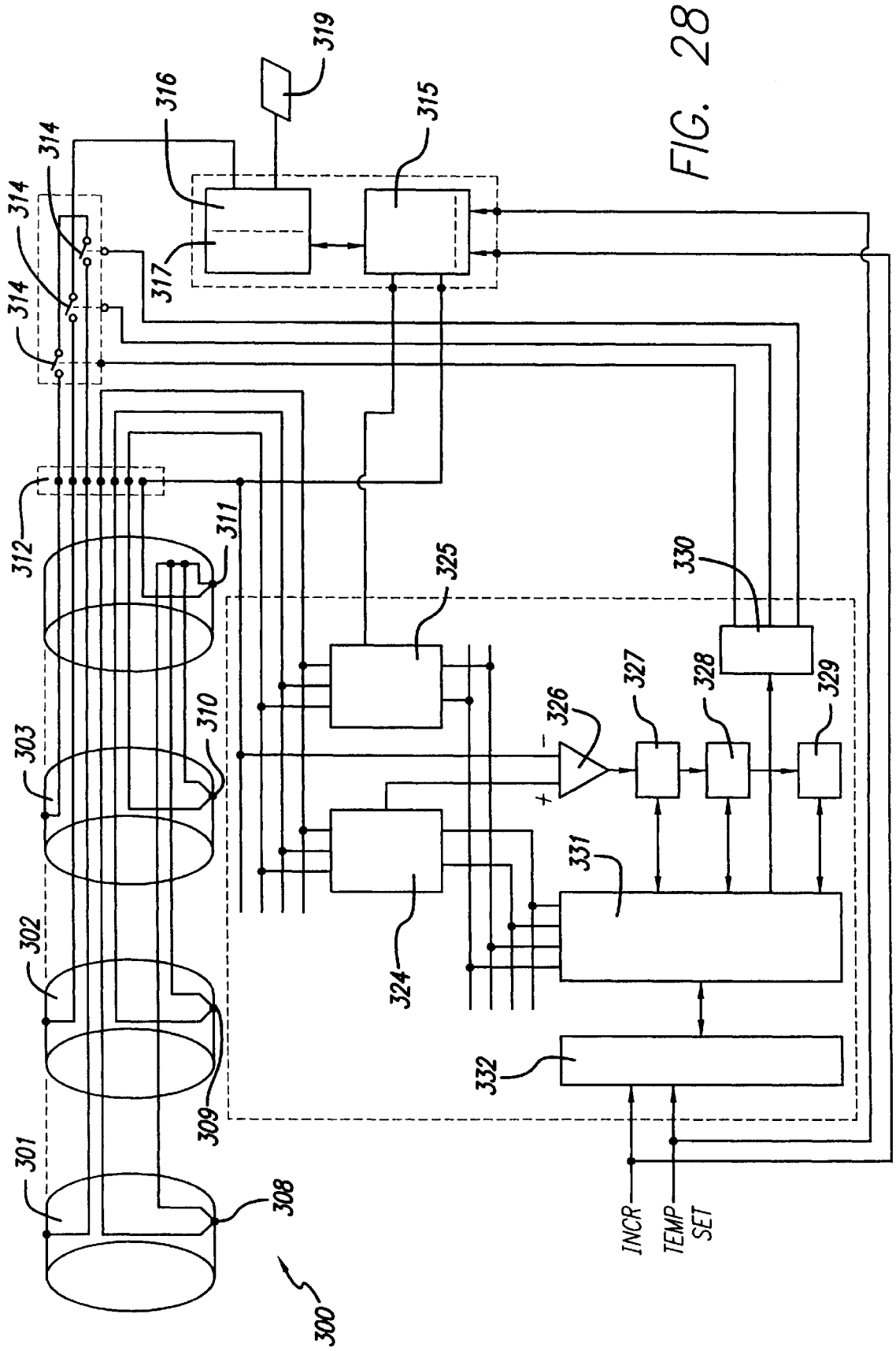
FIGS. 28 and 29 are schematic views of a system for controlling the application of ablating energy to multiple electrodes using multiple temperature sensing inputs.

FIG. 28 shows, in schematic form, a representative system 300 for applying ablating energy by multiple emitters based, at least in part, upon local temperature conditions sensed by multiple sensing elements.

In FIG. 28, the multiple sensing elements comprise thermocouples 308, 309, and 310 individually associated with the multiple emitters of ablating energy, which comprise electrode regions 301, 302, and 303. The system 300 also includes a common reference thermocouple 311 carried within the coupler element for exposure to the blood pool. Alternatively, other kinds of temperature sensing elements can be used, like, for example, thermistors, fluoroptic sensors, and resistive temperature sensors, in which case the reference thermocouple 311 would typically not be required.

The system 300 further includes an indifferent electrode 319 for operation in a uni-polar mode.

The ablating energy emitters 301, 302, 303 can comprise the rigid electrode segments previously described. Alternatively, the electrode regions 301, 302, 303 can comprise a continuous or segmented flexible electrode of wrapped wire or ribbon. It should be appreciated that the system 300 can be used in association with any ablating element that employs multiple, independently actuated ablating elements.

The system 300 includes a source 317 of ablating energy. In FIG. 28, the source 317 generates radio frequency (RF) energy. The source 317 is connected (through a conventional isolated output stage 316) to an array of power switches 314, one for each electrode region 301, 302, and 303. A connector 312 (carried by the probe handle) electrically couples each electrode region 301, 303, 303 to its own power switch 314 and to other parts of the system 300.

The system 300 also includes a microcontroller 331 coupled via an interface 330 to each power switch 314. The microcontroller 331 turns a given power switch 314 on or off to deliver RF power from the source 317 individually to the electrode regions 301, 302, and 303. The delivered RF energy flows from the respective electrode region 301, 302, and 303, through tissue, to the indifferent electrode 319, which is connected to the return path of the isolated output stage 316.

Figure 29:
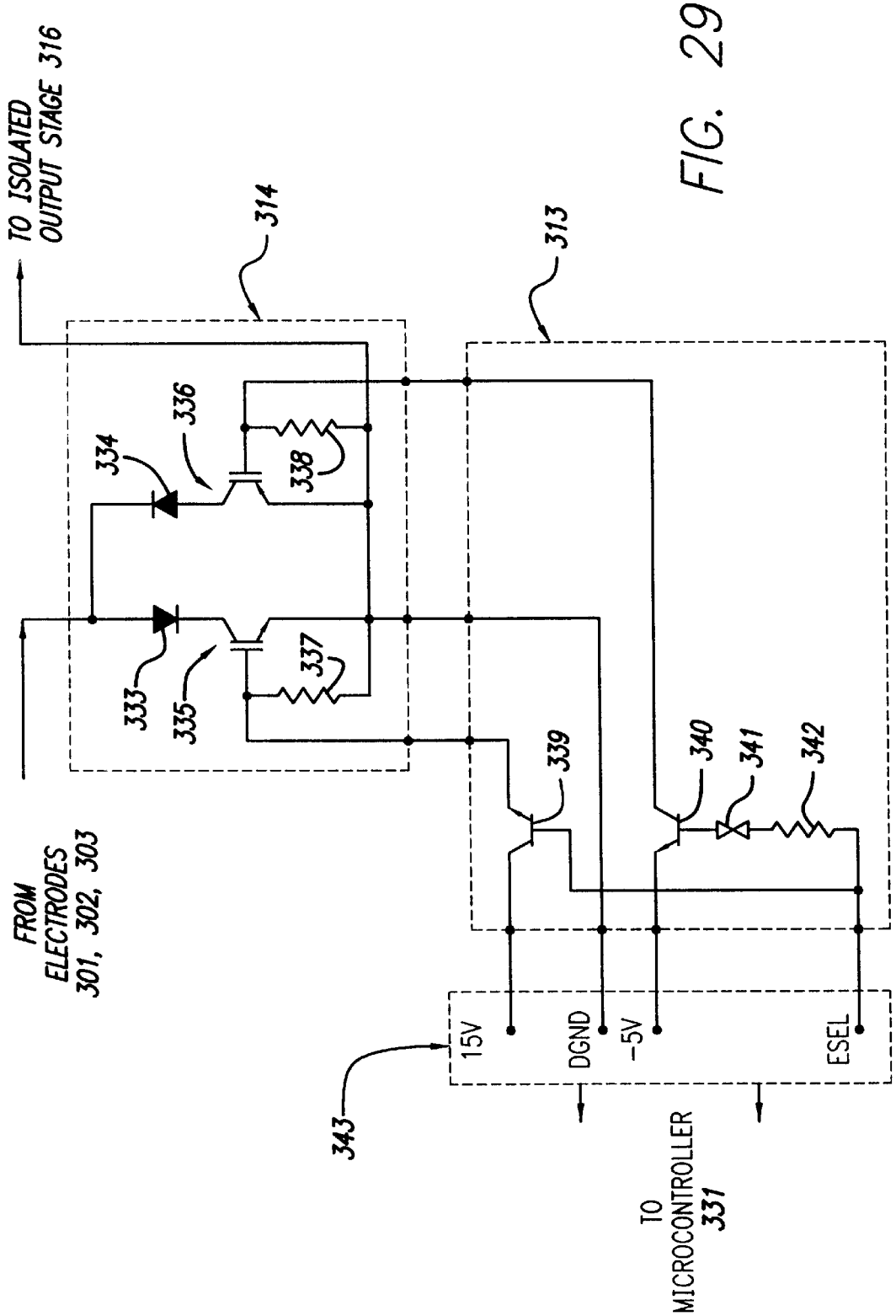

The power switch 314 and interface 330 configuration can vary according to the type of ablating energy being applied. FIG. 29 shows a representative implementation for applying RF ablating energy.

In this implementation, each power switch 314 includes an N-MOS power transistor 335 and a P-MOS power transistor 336 coupled in between the respective electrode region 301, 302, and 303 and the isolated output stage 316 of the power source 317.

A diode 333 conveys the positive phase of RF ablating energy to the electrode region. A diode 334 conveys the negative phase of the RF ablating energy to the electrode region. Resistors 337 and 338 bias the N-MOS and PMOS power transistors 335 and 336 in conventional fashion.

The interface 330 for each power switch 314 includes two NPN transistors 339 and 340. The emitter of the NPN transistor 339 is coupled to the gate of the N-MOS power transistor 335. The collector of the NPN transistor 340 is coupled to the gate of the P-MOS power transistor 380.

The interface for each power switch 314 also includes a control bus 343 coupled to the microcontroller 331. The control bus 343 connects each power switch 314 to digital ground (DGND) of the microcontroller 331. The control bus 343 also includes a (+) power line (+5V) connected to the collector of the NPN transistor 339 and a (−) power line (−5V) connected to the emitter of the NPN interface transistor 340.

The control bus 343 for each power switch 314 further includes an $E_{SEL}$ line. The base of the NPN transistor 339 is coupled to the $E_{SEL}$ line of the control bus 343. The base of the NPN transistor 340 is also coupled the $E_{SEL}$ line of the control bus 343 via the Zener diode 341 and a resistor 332. $E_{SEL}$ line connects to the cathode of the Zener diode 341 through the resistor 332. The Zener diode 341 is selected so that the NPN transistor 340 turns on when $E_{SEL}$ exceeds about 3 volts (which, for the particular embodiment shown, is logic 1).

It should be appreciated that the interface 330 can be designed to handle other logic level standards. In the particular embodiment, it is designed to handle conventional TTL (transistor transfer logic) levels.

The microcontroller 331 sets $E_{SEL}$ of the control bus 343 either at logic 1 or at logic 0. At logic 1, the gate of the N-MOS transistor 335 is connected to (+) 5 volt line through the NPN transistors 339. Similarly, the gate of the PMOS transistor 336 is connected to the (−) 5 volt line through the NPN transistor 340. This conditions the power transistors 335 and 336 to conduct RF voltage from the source 317 to the associated electrode region. The power switch 314 is "on."

When the microcontroller 331 sets $E_{SEL}$ at logic 0, no current flows through the NPN transistors 339 and 340. This conditions the power transistors 335 and 336 to block the conduction of RF voltage to the associated electrode region. The power switch 314 is "off."

The system 300 (see FIG. 28) further includes two analog multiplexers (MUX) 324 and 325. The multiplexers 324 and 325 receive voltage input from each thermocouple 308, 309, 310, and 311. The microcontroller 331 controls both multiplexers 324 and 325 to select voltage inputs from the multiple temperature sensing thermocouples 308, 309, 310, and 311.

The voltage inputs from the thermocouples 308, 309, 310, and 311 are sent to front end signal conditioning electronics. The inputs are amplified by differential amplifier 326, which reads the voltage differences between the copper wires of the thermocouples 308/309/310 and the reference thermocouple 311. The voltage differences are conditioned by element 327 and converted to digital codes by the analog-to-digital converter 328. The look-up table 329 converts the digital codes to temperature codes. The temperature codes are read by the microcontroller 331.

The microcontroller 331 compares the temperature codes for each thermocouple 308, 309, and 310 to preselected criteria to generate feedback signals. The preselected criteria are inputted through a user interface 332. These feedback signals control the interface power switches 314 via the interface 330, turning the electrodes 301, 302, and 303 off and on.

The other multiplexer 325 connects the thermocouples 308, 309, 310, and 311 selected by the microcontroller 331 to a temperature controller 315. The temperature controller 315 also includes front end signal conditioning electronics, as already described with reference to elements 326, 327, 328, and 329. These electronics convert the voltage differences between the copper wires of the thermocouples 308/309/310 and the reference thermocouple 311 to temperature codes. The temperature codes are read by the controller and compared to preselected criteria to generate feedback signals. These feedback signals control the amplitude of the voltage (or current) generated by the source 317 for delivery to the electrodes 301, 302, and 303.

Based upon the feedback signals of the microcontroller 331 and the temperature controller 315, the system 300 distributes power to the multiple electrode regions 301, 302, and 303 to establish and maintain a uniform distribution of temperatures along the ablating element. In this way, the system 300 obtains safe and efficacious lesion formation using multiple emitters of ablating energy.

The system 300 can control the delivery of ablating energy in different ways. Representative modes will now be described.

B. Individual Amplitudes/Collective Duty Cycle

The electrode regions 301, 302, and 303 will be symbolically designated E(J), where J represents a given electrode region (J=1 to N).

As before described, each electrode region E(J) has at least one temperature sensing element 308, 309, and 310, which will be designated S(J,K), where J represents the electrode region and K represents the number of temperature sensing elements on each electrode region (K=1 to M).

In this mode (see FIG. 30), the microcontroller 316 operates the power switch interface 330 to deliver RF power from the source 317 in multiple pulses of duty cycle 1/N.

With pulsed power delivery, the amount of power ($P_{E(J)}$) conveyed to each individual electrode is as follows:

$$P_{E(J)} \sim AMP_{E(J)}^2 \times DUTYCYCLE_{E(J)}$$

where:

$AMP_{E(J)}$ is the amplitude of the RF voltage conveyed to the electrode region E(J), and $DUTYCYCLE_{E(J)}$ is the duty cycle of the pulse, expressed as follows:

$$DUTYCYCLE_{E(J)} = TON_{E(J)}/[TON_{E(J)} + TOFF_{E(J)}]$$

where:

$TON_{E(J)}$ is the time that the electrode region E(J) emits energy during each pulse period, $TOFF_{E(J)}$ is the time that the electrode region E(J) does not emit energy during each pulse period.

The expression $TON_{E(J)} + TOFF_{E(J)}$ represents the period of the pulse for each electrode region E(J).

In this mode, the microcontroller 331 collectively establishes duty cycle ($DUTYCYCLE_{E(J)}$) of 1/N for each electrode region (N being equal to the number of electrode regions).

The microcontroller 331 may sequence successive power pulses to adjacent electrode regions so that the end of the duty cycle for the preceding pulse overlaps slightly with the beginning of the duty cycle for the next pulse. This overlap in pulse duty cycles assures that the source 317 applies power continuously, with no periods of interruption caused by open circuits during pulse switching between successive electrode regions.

In this mode, the temperature controller 315 makes individual adjustments to the amplitude of the RF voltage for each electrode region ($AMP_{E(J)}$), thereby individually changing the power $P_{E(J)}$ of ablating energy conveyed during the duty cycle to each electrode region, as controlled by the microcontroller 331.

In this mode, the microcontroller 331 cycles in successive data acquisition sample periods. During each sample period, the microcontroller 331 selects individual sensors S(J,K), and voltage differences are read by the controller 315 (through MUX 325) and converted to temperature codes TEMP(J).

When there is more than one sensing element associated with a given electrode region, the controller 315 registers all sensed temperatures for the given electrode region and selects among these the highest sensed temperature, which constitutes TEMP(J).

In this mode, the controller 315 compares the temperature TEMP(J) locally sensed at each electrode E(J) during each data acquisition period to a set point temperature $TEMP_{SET}$ established by the physician. Based upon this comparison, the controller 315 varies the amplitude $AMP_{E(J)}$ of the RF voltage delivered to the electrode region E(J), while the microcontroller 331 maintains the $DUTYCYCLE_{E(J)}$ for that electrode region and all other electrode regions, to establish and maintain TEMP(J) at the set point temperature TEMP$_{SET}$.

The set point temperature TEMP$_{SET}$ can vary according to the judgment of the physician and empirical data. A representative set point temperature for cardiac ablation is believed to lie in the range of 40° C. to 95° C., with 70° C. being a representative preferred value.

The manner in which the controller 315 governs AMP$_{E(J)}$ can incorporate proportional control methods, proportional integral derivative (PID) control methods, or fuzzy logic control methods.

For example, using proportional control methods, if the temperature sensed by the first sensing element TEMP(1) >TEMP$_{SET}$, the control signal generated by the controller 315 individually reduces the amplitude AMP$_{E(1)}$ of the RF voltage applied to the first electrode region E(1), while the microcontroller 331 keeps the collective duty cycle DUTYCYCLE$_{E(1)}$ for the first electrode region E(1) the same. If the temperature sensed by the second sensing element TEMP(2)<TEMP$_{SET}$, the control signal of the controller 315 increases the amplitude AMP$_{E(2)}$ of the pulse applied to the second electrode region E(2), while the microcontroller 331 keeps the collective duty cycle DUTYCYCLE$_{E(2)}$ for the second electrode region E(2) the same as DUTYCYCLE$_{E(1)}$, and so on. If the temperature sensed by a given sensing element is at the set point temperature TEMP$_{SET}$, no change in RF voltage amplitude is made for the associated electrode region.

The controller 315 continuously processes voltage difference inputs during successive data acquisition periods to individually adjust AMP$_{E(J)}$ at each electrode region E(J), while the microcontroller 331 keeps the collective duty cycle the same for all electrode regions E(J). In this way, the mode maintains a desired uniformity of temperature along the length of the ablating element.

Using a proportional integral differential (PID) control technique, the controller 315 takes into account not only instantaneous changes that occur in a given sample period, but also changes that have occurred in previous sample periods and the rate at which these changes are varying over time. Thus, using a PID control technique, the controller 315 will respond differently to a given proportionally large instantaneous difference between TEMP (J) and TEMP$_{SET}$, depending upon whether the difference is getting larger or smaller, compared to previous instantaneous differences, and whether the rate at which the difference is changing since previous sample periods is increasing or decreasing.

C. Deriving Predicted Hottest Temperature

Because of the heat exchange between the tissue and the electrode region, the temperature sensing elements may not measure exactly the maximum temperature at the region. This is because the region of hottest temperature occurs beneath the surface of the tissue at a depth of about 0.5 to 2.0 mm from where the energy emitting electrode region (and the associated sensing element) contacts the tissue. If the power is applied to heat the tissue too quickly, the actual maximum tissue temperature in this subsurface region may exceed 100° C. and lead to tissue desiccation and/or micro-explosion.

Figure 31:
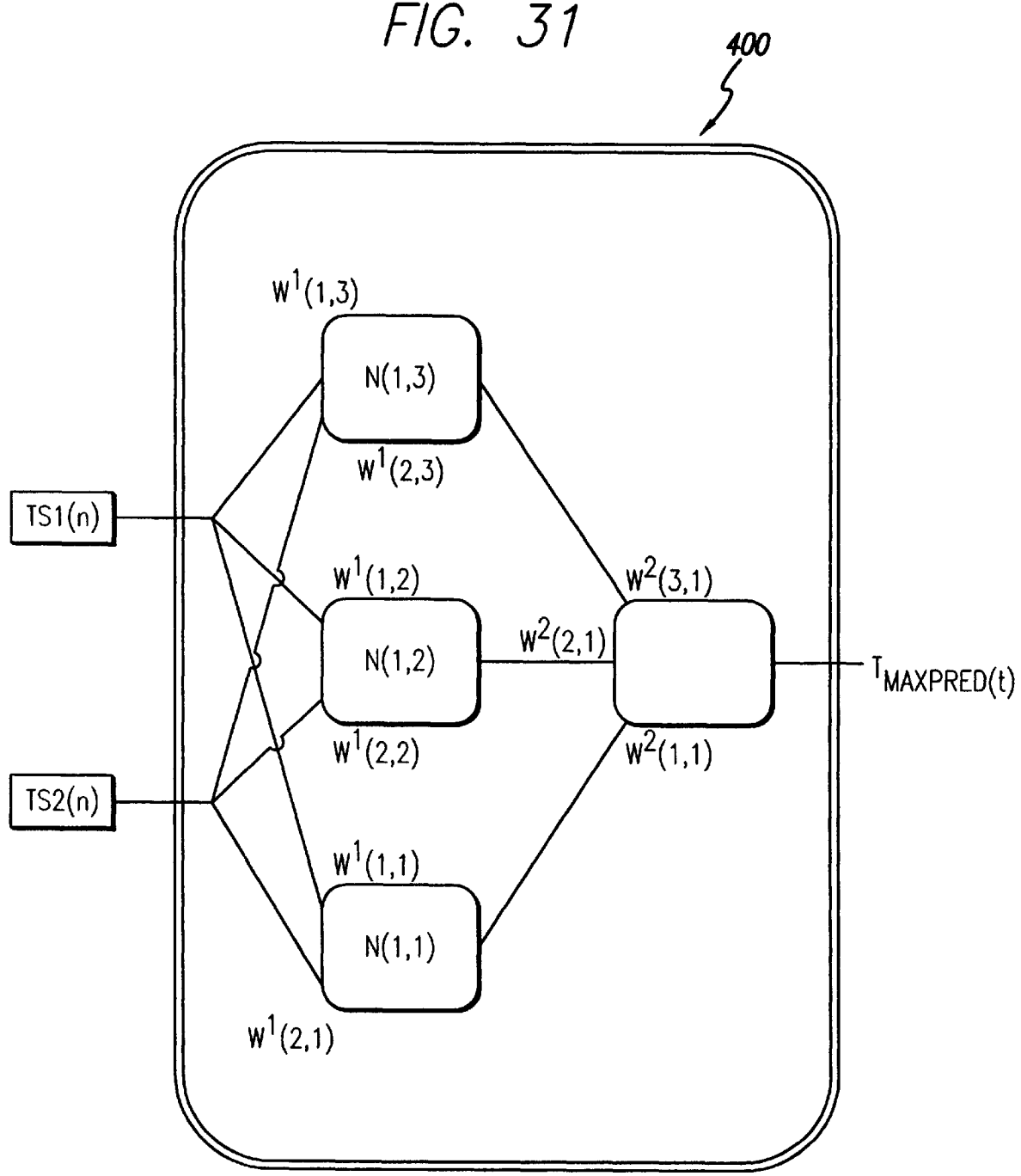
FIG. 31 is a schematic view of a neural network predictor, which receives as input the temperatures sensed by multiple sensing elements at a given electrode region and outputs a predicted temperature of the hottest tissue region.

FIG. 31 shows an implementation of a neural network predictor 400, which receives as input the temperatures sensed by multiple sensing elements S(J,K) at each electrode region, where J represents a given electrode region (J=1 to N) and K represents the number of temperature sensing elements on each electrode region (K=1 to M). The predictor 400 outputs a predicted temperature of the hottest tissue region T$_{MAXPRED}$(t). The controller 315 and microcontroller 331 derive the amplitude and duty cycle control signals based upon T$_{MAXPRED}$(t), in the same manners already described using TEMP(J).

Figure 30:
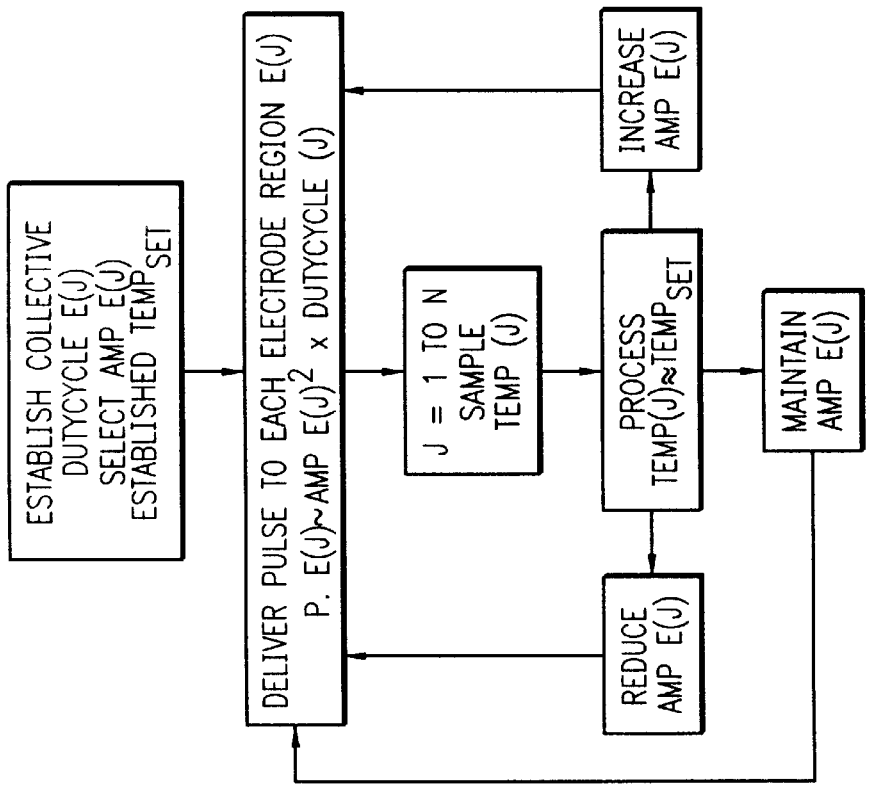
FIG. 30 is a schematic flow chart showing an implementation of the temperature feedback controller shown in FIGS. 28 and 29, using individual amplitude control with collective duty cycle control.

The predictor 400 uses a two-layer neural network, although more hidden layers could be used. As shown in FIG. 30, the predictor 400 includes a first and second hidden layers and four neurons, designated N$_{(L,X)}$, where L identifies the layer 1 or 2 and X identifies a neuron on that layer. The first layer (L=1) has three neurons (X=1 to 3), as follows N$_{(1,1)}$; N$_{(1,2)}$; and N$_{(1,3)}$. The second layer (L=2) comprising one output neuron (X=1), designated N$_{(2,1)}$.

Temperature readings from the multiple sensing elements, only two of which—TS1(n) and TS2(n)—are shown for purposes of illustration, are weighed and inputted to each neuron N$_{(1,1)}$; N$_{(1,2)}$; and N$_{(1,3)}$ of the first layer. FIG. 31 represents the weights as W$^L_{(k,N)}$, where L=1; k is the input sensor order; and N is the input neuron number 1, 2, or 3 of the first layer.

The output neuron N$_{(2,1)}$ of the second layer receives as inputs the weighted outputs of the neurons N$_{(1,1)}$; N$_{(1,2)}$; and N$_{(1,3)}$. FIG. 30 represents the output weights as W$^L_{(O,X)}$, where L=2; O is the output neuron 1, 2, or 3 of the first layer; and X is the input neuron number of the second layer. Based upon these weighted inputs, the output neuron N$_{(2,1)}$ predicts T$_{MAXPRED}$(t). Alternatively, a sequence of past reading samples from each sensor could be used as input. By doing this, a history term would contribute to the prediction of the hottest tissue temperature.

The predictor 400 must be trained on a known set of data containing the temperature of the sensing elements TS1 and TS2 and the temperature of the hottest region, which have been previously acquired experimentally. For example, using a back-propagation model, the predictor 400 can be trained to predict the known hottest temperature of the data set with the least mean square error. Once the training phase is completed the predictor 400 can be used to predict T$_{MAXPRED}$(t).

Other types of data processing techniques can be used to derive T$_{MAXPRED}$(t). See, e.g., co-pending patent application Ser. No. 08/266,934, filed Jun. 27, 1994, and entitled "Tissue Heating and Ablation Systems and Methods Using Predicted Temperature for Monitoring and Control."

The illustrated and preferred embodiments used digital processing controlled by a computer to analyze information and generate feedback signals. It should be appreciated that other logic control circuits using microswitches, AND/OR gates, invertors, analog circuits, and the like are equivalent to the micro-processor controlled techniques shown in the preferred embodiment.

Although the present invention has been described in terms of the preferred embodiments above, numerous modifications and/or additions to the above-described preferred embodiments would be readily apparent to one skilled in the art. It is intended that the scope of the present invention extends to all such modifications and/or additions and that the scope of the present invention is limited solely by the claims set forth below.

Additionally, this specification discloses multiple electrode structures in the context of cardiac ablation because the structures are well suited for use in the field of cardiac ablation. Nevertheless, it should be appreciated that the disclosed structures are applicable for use in other applications. For example, various aspects of the invention have applications and procedures concerning other regions of the body such as the prostate, brain, gall bladder and uterus.

We claim:

1. A surgical device, comprising:
a relatively short malleable shaft defining a distal end and a proximal end;
a bendable spline assembly connected to the distal end of the shaft and having a predetermined configuration, the spline assembly being adapted to collapse in response to an application of an external force and to expand to the predetermined configuration in response to a withdrawal of the external force; and
an operative element associated with the bendable spline assembly.

2. A surgical device as claimed in claim 1, further comprising:
a substantially tubular member positioned around the shaft and slidable relative to the shaft;
wherein the spline assembly is adapted to collapse in response to movement of the substantially tubular member thereover and to expand to the predetermined configuration in response to a retraction of the substantially tubular member.

3. A surgical device as claimed in claim 2, wherein the substantially tubular member comprises a substantially cylindrical member.

4. A surgical device as claimed in claim 2, wherein the substantially tubular member comprises a sheath.

5. A surgical device as claimed in claim 2, wherein the tubular member is relatively stiff.

6. A surgical device as claimed in claim 2, wherein the tubular member is malleable.

7. A surgical device as claimed in claim 2, wherein the tubular member is somewhat flexible.

8. A surgical device as claimed in claim 2, wherein the tubular member defines a bending modulus between 3 lb.-in.$^2$ and 50 lb.-in.$^2$.

9. A surgical device as claimed in claim 1, wherein the bendable spline assembly includes a substantially annular portion.

10. A surgical device as claimed in claim 1, wherein the operative element comprises an electrode.

11. A surgical device as claimed in claim 1, wherein the operative element comprises a plurality of electrodes.

12. A surgical device as claimed in claim 1, wherein the operative element comprises an energy emitting element.

13. A surgical device as claimed in claim 1, further comprising:
a handle associated with the proximal end of the shaft.

14. A surgical device as claimed in claim 1, wherein the shaft defines an overall length and the overall length is less than approximately 20 inches.

15. A surgical device as claimed in claim 1, wherein the shaft defines a bending modulus between 3 lb.-in.$^2$ and 50 lb.-in.$^2$.

16. A surgical device as claimed in claim 1, wherein the bendable spline assembly is in the form of a loop.

17. A surgical device as claimed in claim 1, wherein the bendable spline assembly comprises a spring member having a cross-section defining a length and a width, and the length is different than the width.

18. A surgical device as claimed in claim 1, wherein the bendable spline assembly comprises a spring member is in the form of a loop, the loop defining a plane and being adapted to bend in response to an in-plane force and resist bending in response to an equal out-of-plane force.

19. A surgical device as claimed in claim 1, further comprising:
a steering element operably connected to the bendable spline assembly.

20. A surgical device, comprising:
a relatively short shaft defining a distal end, a proximal end and a longitudinal axis;
a bendable spline assembly associated with the distal end of the shaft and having a substantially annular portion that lies in a plane oriented substantially perpendicular to the longitudinal axis and having a predetermined configuration, the spline assembly being adapted to collapse in response to an application of an external force and to expand to the predetermined configuration in response to a withdrawal of the external force; and
a plurality of circumferentially spaced electrodes carried by the annular portion of the spline assembly.

21. A surgical device, comprising:
a relatively short shaft defining a distal end, a proximal end and an overall length less than approximately 20 inches;
a substantially triangularly-shaped spline assembly associated with the distal end of the shaft and having a predetermined configuration, the spline assembly being adapted to collapse in response to an application of an external force and to expand to the predetermined configuration in response to a withdrawal of the external force; and
a plurality of spaced electrodes carried by the bendable spline assembly.

22. A surgical device as claimed in claim 21, wherein the substantially triangularly-shaped spline assembly comprises a distal leg defining first and second ends, the distal leg being non-linear from the first end to the second end.

23. A surgical device as claimed in claim 22, wherein the distal leg comprises a first linear portion, a second linear portion and a non-linear portion therebetween.

24. A surgical device as claimed in claim 23, wherein the first linear portion defines a first length, the second linear portion defines a second length, and the first length is equal to the second length.

25. A surgical device as claimed in claim 21, wherein the substantially triangularly-shaped spline assembly comprises a distal leg, a first side leg and a second side leg, and at least one of the first and second side legs includes a guidewire.

* * * * *